(12) United States Patent
Hundley et al.

(10) Patent No.: US 8,660,327 B2
(45) Date of Patent: Feb. 25, 2014

(54) WORKSTATIONS WITH CIRCUITS FOR GENERATING IMAGES OF GLOBAL INJURY

(75) Inventors: William Gregory Hundley, Winston-Salem, NC (US); Craig A. Hamilton, Lewisville, NC (US); Ralph B. D'Agostino, Winston-Salem, NC (US)

(73) Assignee: Wake Forest University Health Sciences, Winston-Salem, NC (US)

(*) Notice: Subject to any disclaimer, the term of this patent is extended or adjusted under 35 U.S.C. 154(b) by 181 days.

(21) Appl. No.: 13/315,970

(22) Filed: Dec. 9, 2011

(65) Prior Publication Data
US 2012/0082352 A1 Apr. 5, 2012

Related U.S. Application Data

(60) Continuation of application No. 13/029,380, filed on Feb. 17, 2011, now Pat. No. 8,103,073, which is a division of application No. 11/626,958, filed on Jan. 25, 2007, now Pat. No. 7,907,759, which is a continuation-in-part of application No. 12/019,457, filed on Jan. 24, 2008, now Pat. No. 8,532,739, application No. 13/315,970, which is a continuation of application No. 11/051,304, filed on Feb. 4, 2005, now Pat. No. 7,333,845.

(60) Provisional application No. 60/764,469, filed on Feb. 2, 2006, provisional application No. 60/542,547, filed on Feb. 6, 2004.

(51) Int. Cl.
*G06K 9/00* (2006.01)

(52) U.S. Cl.
USPC .......................................................... 382/128

(58) Field of Classification Search
USPC .......................... 382/128–134; 128/920–925; 356/39–49; 600/407–414, 424–426; 345/581–618; 250/455
See application file for complete search history.

(56) References Cited

U.S. PATENT DOCUMENTS

| 5,233,299 | A | 8/1993 | Souza et al. |
| 5,333,244 | A | 7/1994 | Harashima |
| 5,732,121 | A | 3/1998 | Takeo et al. |
| 5,871,013 | A | 2/1999 | Wainer et al. |
| 6,368,285 | B1 | 4/2002 | Osadchy et al. |

(Continued)

FOREIGN PATENT DOCUMENTS

| JP | 2003-325458 | 11/2003 |
| WO | WO01/87173 | 11/2001 |

(Continued)

OTHER PUBLICATIONS

Jirak, Daniel, et al., Texture Analysis of Human Liver, Journal of Magnetic Resonance Imaging, vol. 15, pp. 68-74, 2002.

(Continued)

*Primary Examiner* — Atiba O Fitzpatrick
(74) *Attorney, Agent, or Firm* — Myers Bigel Sibley & Sajovec, P.A.

(57) ABSTRACT

Physician interactive workstations with global voxel distribution visualization may also include one or more of a 3-D color scale image of a population of voxel in target regions, organs or systems. The workstation may be configured to evaluate intensity or other measures of voxels of patient images associated with tissue for early detection of a global injury.

24 Claims, 34 Drawing Sheets

(56) References Cited

U.S. PATENT DOCUMENTS

| | | |
|---|---|---|
| 6,415,046 B1 | 7/2002 | Kerut, Sr. |
| 7,106,892 B2 | 9/2006 | Breeuwer et al. |
| 7,187,789 B2 | 3/2007 | Takeo |
| 7,258,670 B2 | 8/2007 | Bardy |
| 7,301,016 B2 | 11/2007 | Meyers et al. |
| 7,330,601 B2 | 2/2008 | Shin et al. |
| 7,333,845 B2 | 2/2008 | Hundley et al. |
| 7,396,654 B2 | 7/2008 | Hayes et al. |
| 7,747,308 B2 | 6/2010 | Hundley et al. |
| 2003/0009098 A1 | 1/2003 | Jack et al. |
| 2003/0063787 A1 | 4/2003 | Natanzon et al. |
| 2005/0075567 A1 | 4/2005 | Skyba et al. |
| 2005/0215883 A1 | 9/2005 | Hundley et al. |

FOREIGN PATENT DOCUMENTS

| | | |
|---|---|---|
| WO | WO03/061466 | 7/2003 |
| WO | WO 2004/026140 | 4/2004 |
| WO | WO 2005/077263 | 8/2005 |

OTHER PUBLICATIONS

"General Principals of Software Validation; Final Guidance for Industry and FDA Staff" U.S. Dept of Health and Human Services, Food and Drug Administration, Center for Devices and Radiological Health, Center for Biologics and Evaluation Research, 47 pages (Jan. 11, 2002).

Able Software Corp., XP-002449130, *3D-Doctor Overview and Tutorial*, pp. 15-129, Oct. 16, 2003.

Bellenger et al. "Reduction in Sample Size for Studies of Remodeling in Heart Failure by the Use of Cardiovascular Magnetic Resonance" *J Cardiovascular Mangn Reson* 2(4): 271-278 (2000) (Abstract).

Bristow et al. "Doxorubicin Cardiomyopathy: Evaluation by Phonocardiography, Endomyocardial Biopsy, and Cardiac Catheterization" *Annals of Internal Medicine* 88: 168-175 (1978).

Cardinale et al. "Myocardial Injury Revealed by Plasma Troponin I in Breast Cancer Treated with High-Dose Chemotherapy" *Annals of Oncology* 13: 710-715 (2002).

Cerqueira et al. "Standardized Myocardial Segmentation and Nomenclature for Tomographic Imaging of the Heart: A Statement for Healthcare Professionals from the Cardiac Imaging Committee of the Council on Clincial Cardiology of the American Heart Association" *Circulation* 150: 539-542 (2002).

Choi et al. "Transmural Extent of Acute Myocardial Infarction Predicts Long-Term Improvement in Contractile Function" *Circulation* 104: 1101-1107 (2001).

Chuang et al. "Importance of Imaging Method Over Imaging Modality in Noninvasive Determination of Left Ventricular Volumes and Ejection Fraction: Assessment by Two- and Three-Dimensional Echocardiography and Magnetic Resonance Imaging" *Journal of the American College of Cardiology* 35(2): 477-484 (2000).

Darty et al. "Nursing Responsibilities During Cardiac Magnetic Resonance Imaging" Department of Internal Medicine (Cardiology Section) and Radiology at the Wake Forest University School of Medicine (no date, but believed to be before Feb. 6, 2004).

Del Carlo et al. "Cardiac Troponins in Congestive Heart Failure" *American Heart Journal* 138: 646-653 (1999).

Dombernowsky et al. "Doxorubicin and Paclitaxel, a Highly Active Combination in the Treatment of Metastatic Breast Cancer" *Seminars in Oncology* 23(5 suppl 11): 23-27 (1996).

Gehl et al. "Paclitaxel and Doxorubicin in Metastatic Breast Cancer" *Seminars in Oncology* 23(6 suppl 15): 35-38 (1996).

Gerber et al. "Relation Between GD-DTPA Contrast Enhancement and Regional Inotropic Response in the Periphery and Center of Myocardial Infarction" *Circulation* 104:998-1004 (2001).

Gerber et al. "Accuracy of contrast-enhanced magnetic resonance imaging in predicting improvement of regional myocardial function in patients after acute myocardial infarction", Circulation, vol. 106, No. 9, pp. 1083-1089, (Aug. 27, 2002).

Gianni et al. "Cardiac Function Following Combination Therapy with Taxol (T) and Doxorubicin (A) for Advanced Breast Cancer (ABC)" *Proceedings of ASCO* vol. 17 (1998) (Abstract).

Gianni et al. "Paclitaxel by 3-Hour Infusion in Combination with Bolus Doxorubicin in Women with Untreated Metastatic Breast Cancer: High Antitumor Efficacy and Cardiac Effects in a Dose-Finding and Sequence-Finding Study" *Journal of Clinical Oncology* 13(11): 2688-2699 (1995).

Gottdiener et al. "Doxorubicin Cardiotoxicity: Assessment of Late Left Ventricular Dysfunction by Radionuclide Cineangiography" *Annals of Internal Medicine* 94(part 1): 430-435 (1981).

Hamilton et al. "Is Imaging at Intermediate Doses Necessary During Dobutamine Stress Magnetic Resonance Imaging?" *Journal of Cardiovascular Magnetic Resonance* 3(4): 297-302 (2001).

Heiberg, E., XP-002449063, Automated Feature Detection in Multidimensional Images, pp. 1-149, Linköping Dec. 2004.

Hochster et al. "Cardiotoxicity and Cardioprotection During Chemotherapy" *Current Science* 7: 304-309 (1995).

Hortobagyi "Treatment of Breast Cancer" *The New England Journal of Medicine* 339(14): 974-984(1998).

Hundley et al. "Magnetic Resonance Imaging Determination of cardiac Prognosis" *Circulation* 106: 2328-2333 (2002).

Hundley et al. "Magnetic Resonance Imaging Assessment of the Severity of Mitral Regurgitation: Comparison with Invasive Techniques" *Circulation* 92: 1151-1158 (1995).

Hundley et al. "Relation of Cardiac Prognosis to Segment Location with Apical Left Ventricular Ischemia" *The American Journal of Cardiology* 92: 1206-1208 (2003).

Hundley et al. "Utility of Fast Cine Magnetic Resonance Imaging an display for the Detection of Myocardial Ischemia in patients Not Well Suited for Second Harmonic Stress Echocardiography" *Circulation* 100: 1697-1702 (1999).

International Search Report and Written Opinion for PCT/US2006/003763; mailed May 30, 2005.

International Search Report and Written Opinion dated Sep. 12, 2007 for corresponding PCT application No. PCT/US2007/001927.

Jacobson et al. "Magnetic Resonance Imaging of the Cardiovascular System: Present State of the Art and Future Potential" *JAMA* 259(2): 253-259 (1988).

Jensen et al. "Functional Monitoring of Anthracycline Cardiotoxicity: A Prospective, Blinded, Long-Term Observational Study of Outcome in 120 Patients" *Annals of Oncology* 13: 699-709 (2002).

Judd et al. "Physiological basis of Myocardial Contrast Enhancement in Fast Magnetic Resonance Images of 2-Day-Old Reperfused Canine Infarcts" *Circulation* 92: 1902-1910 (1995).

Kellman et al. "Phase-Sensitive Inversion Recover for Detecting Myocardial Infarction Using Gadolinium-Delayed Hyperenhancement" *Magnetic Resonance in Medicine* 47: 372-383 (2002).

Kim et al. "The Use of Contract-Enhanced Magnetic Resonance Imaging to Identify Reversible Myocardial Dysfunction" *New England Journal of Medicine* 343: 1445-1453 (2000).

Leandro et al. "Cardiac Dysfunction Late After Cardiotoxic Therapy for Childhood Cancer" *The American Journal of Cardiology* 74:1152-1156 (1994).

Lebwhol et al. "New Developments in Chemotherapy of Advanced Breast Cancer" *Annals of Oncology* 10(suppl 6): S139-S146 (1999).

Lipshultz et al. "Late Cardiac Effects of Doxorubicin Therapy for Acute Lymphoblastic Leukemia in Childhood" *The New England Journal of Medicine* 324(12): 808-815 (1991).

Longmore et al. "Dimensional Accuracy of Magnetic Resonance in Studies of the Heart" *The Lancet* pp. 1360-1362 (Jun. 15, 1985).

Lorenz et al. "Normal Human Right and Left Ventricular Mass, Systolic Function, and Gender Differences by Cine Magnetic Resonance Imaging" *J Cardiovascular Magn Reson* 1(1): 7-21 (1999) (Abstract).

Maisel et al. "B-Type Natriuretic Peptide Levels: Diagnostic and Prognostic in Congestive Heart Failure: What's Next?" *Circulation* 150: 2328-2331 (2002).

Martin et al. "Imaging Cardiac Structure and Pump Function" *Cardiac Magnetic Resonance Imaging* 16(2): 135-160 (1998).

McDonagh et al. "Biochemical Detection of Left-Ventricular Systolic Dysfunction" *The Lancet* 351: 9-13 (1998).

(56) References Cited

OTHER PUBLICATIONS

Missov et al. "Cardiac Troponin I in Patients with Hematologic Malignancies" *Coronary Artery Disease* 8: 537-541 (1997).
Osoba et al. "Effects on Quality of Life of Combined Trastuzumab and Chemotherapy in women with Metastatic Breast Cancer" *Journal of Clinical Oncology* 20(14): 3106-3113 (2002).
Pagani et al. "Dose-Finding Study of Epidoxorubicin and Docetaxel as First-Line Chemotherapy in Patients with Advanced Breast Cancer" *Annals of Oncology* 10: 539-545 (1999).
Pattynama et al. "Left Ventricular Measurements with Cine and Spin-Echo MR Imaging: A Study of Reproducibility with Variance Component Analysis" *Radiology* 187: 261-268 (1993).
Rector et al. "Assessment of Patient Outcome with the Minnesota Living Heart Failure Questionnaire: Reliability and Validity During Randomized, Double-Blind, Placebo-Controlled Trial of Pimobendan" *American Heart Journal* 124: 1017-1025 (1992).
Rehr et al. "Left Ventricular Volumes Measured by MR Imaging" *Radiology* 156: 717-719 (1985).
Rerkpattanapipat et al. "Clinical Utility of Assessments of Left Ventricular Systolic Function and Coronary Arterial Blood Flow During Pharmacological Stress with Magnetic Resonance Imaging" *Topics in Magnetic Resonance Imaging* 11(6): 399-405 (2000).
Rischin et al. "A Phase I and Pharmacokinetic Study of Paclitaxel and Epirubicin in Advanced Cancer" *Investigational New Drugs* 17: 73-80 (1999).
Saeed M et al., "Reversible and irreversible injury in the reperfused myocardium: differentiation with contrast material-enhanced MR imaging", Radiology, Oak Brook, IL, US, vol. 175, No. 3, pp. 633-637, (Apr. 1990).
Schwartz et al. "Congestive Heart Failure and Left Ventricular Dysfunction Complicating Doxorubicin Therapy" *The American Journal of Medicine* 82: 1109-1118 (1987).
Sechetem et al. "Measurement of Right and Left Ventricular Volumes in healthy Individuals with cine MR Imaging" *Radiology* 163: 697-702 (1987).
Semelka et al. "Interstudy Reproducibility of Dimensional and Functional Measurements Between Cine Magnetic Resonance Studies in the Morphologically Abnormal Left Ventricle" *American Heart Journal* 119: 1367-1373 (1990).
Shek et al. "Paclitaxel-Induced Cardiotoxicity" *Arch Pathol Lab Med* 120: 89-91 (1996).
Singal et al. "Doxorubicin-Induced Cardiomyopathy" *The New England Journal of Medicine* 339(13): 900-905 (1998).
Slamon et al. "Use of Chemotheraphy Plus a Monocolonal Antibody Against Her2 for Matastatic Breast Cancer that Overrexpresses Her2" *The New England Journal of Medicine* 344(11): 783-792 (2001).
Stratemeier et al. "Ejection Fraction Determination by MR Imaging: Comparison with Left Ventricular Angiography" *Radiology* 158: 775-777 (1986).
Suter et al. "Detection of Anthracycline-Induced Cardiotoxicity: Is There Light at the End of the Tunnel?" *Annals of Oncology* 13: 647-649 (2002).
Torti et al. "Cardotoxicity of Epirubicin and Doxorubicin: Assessment by Endomyocardial Biopsy" *Cancer Research* 46: 3722-3727 (1986).
Torti et al. "Weekly Doxorubicin in Endocrine-Refractory Carcinoma of the Prostate" *Journal of Clinical Oncology* 1(8): 477-482 (1983).
Unverferth et al. "Early Changes in Human Myocardial Nuclei after Doxorubicin" *Cancer* 52:215-221 (1983).
Valdivieso et al. "Increased Therapeutic Index of Weekly Doxorubicin in the Therapy of Non-Small Cell Lung Cancer: A Prospective, Randomized Study" *Journal of Clinical Oncology* 2(3): 207-214 (1984).
Von Hoff et al. "Daunomycin-Induced Cardiotoxicity in Children and Adults" *The American Journal of Medicine* 62:200-208 (1977).
Von Hoff et al. "Risk Factors for Doxorubicin-Induced Congestive Heart Failure" *Annals of Internal Medicine* 91: 710-77 (1979).
Wassmuth et al., "Subclinical cardiotoxic effects of anthracyclines as assessed by magnetic resonance imaging—A pilot study", American Heart Journal, Jun. 2001, vol. 141, No. 6, pp. 1007-1013, (Jun. 2001).
Wu et al. "Visualisation of Presence, Location, and Transmural Extent of Healed Q-Wave and Non-Q-Wave Myocardial Infarction" *The Lancet* 357: 21-28 (2001).
Herlidou-Meme, S. et al., MRI texture analysis on texture test objects, normal brain and intracranial tumors, Magnetic Resonance Imaging, 2003, pp. 989-993, vol. 21.
Sakuma, et al., Functional MRI diagnosis for heart, New Medical Care, Jun. 11, 2001, vol. 28, No. 6, pp. 50-53. (Translation of excerpts).

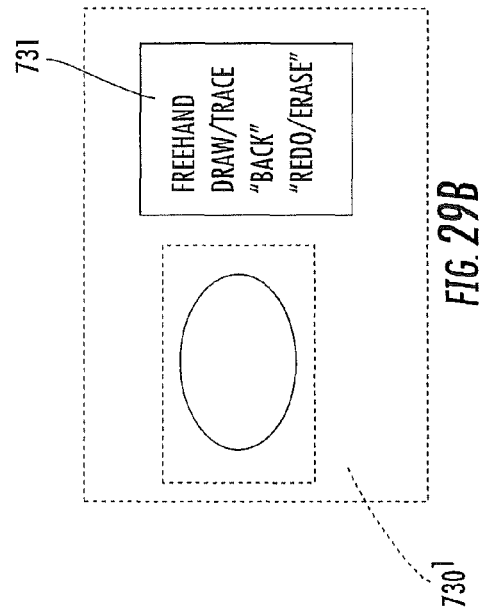
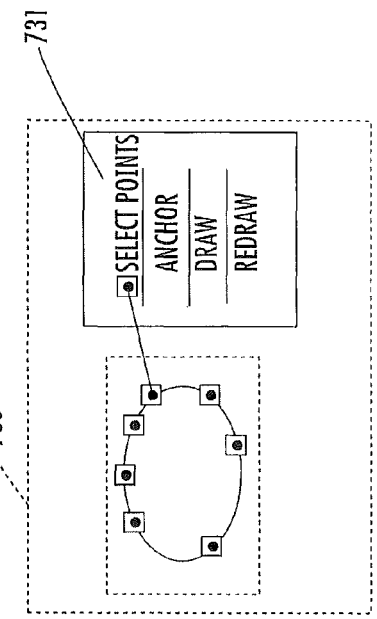
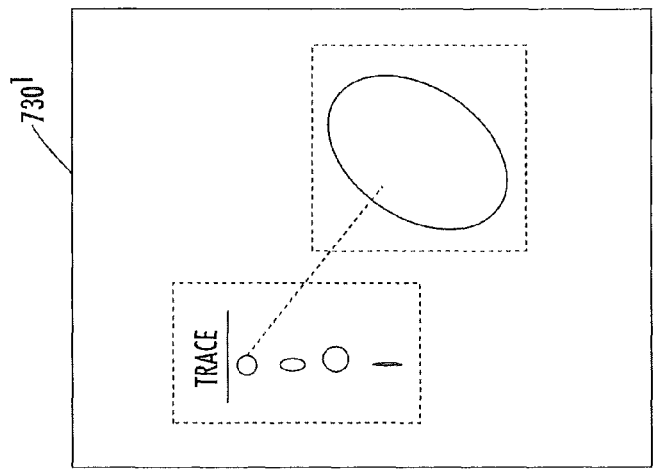
FIG. 29B
FIG. 29C
FIG. 29A

WORKSTATIONS WITH CIRCUITS FOR GENERATING IMAGES OF GLOBAL INJURY

RELATED APPLICATIONS

This application is a continuation-in-part of U.S. patent application Ser. No. 12/019,457, filed Jan. 24, 2008 now U.S. Pat. No. 8,532,739, which is a continuation of U.S. patent application Ser. No. 11/051,304, filed Feb. 4, 2005, which issued as U.S. Pat. No. 7,333,845 on Feb. 19, 2008, which claims the benefit of priority of U.S. Provisional Patent Application Ser. No. 60/542,547 filed Feb. 6, 2004, the entire contents of the above-referenced documents are hereby incorporated herein by reference as if recited in full herein.

This application is also a continuation of U.S. patent application Ser. No. 13/029,380, filed Feb. 17, 2011 now U.S. Pat. No. 8,103,073, which is a divisional of U.S. patent application Ser. No. 11/626,958, filed Jan. 25, 2007, which issued as U.S. Pat. No. 7,907,759 on Mar. 15, 2011, which claims priority claims priority to U.S. Provisional Application Ser. No. 60/764,469, filed Feb. 2, 2006, the entire contents of the above-referenced documents are hereby incorporated herein by reference as if recited in full herein.

FIELD OF THE INVENTION

The present invention is related to diagnostics and more particularly to evaluation of image data to detect tissue injury and/or a change in a tissue property.

BACKGROUND OF THE INVENTION

Cancer treatments typically include radiation and/or chemotherapies. The chemotherapies can include one or a combination of cytotoxic agents and/or antineoplastics such as alkylating agents, nitrogen mustards, nitrosureas, antibiotics, hormonal antagonists or androgens, antiandrogens, antiestrogens, estrogen/nitrogen mixtures, estrogens, gonadotroopin releasing hormones, immunomodulators, and other appropriate therapeutic agents.

Doxorubicin is an anthracycline antibiotic isolated from a soil microorganism. Its anti-tumor effects are related to interactions with the enzyme topoisomerase-2 and production of double strand DNA breaks. In addition, this agent generates intracellular free radicals that are highly cytotoxic. Doxorubicin is considered one of the most broadly active antitumor agents. Not only is doxorubicin typically considered an important element in modern therapy of breast, soft tissue sarcomas and other solid tumors, it is thought to be an important element of curative combination chemotherapy for acute leukemia, Hodgkin's disease, non-Hodgkin's lymphoma, and many childhood cancers. Thus, for many individuals with advanced stages of cancer, doxorubicin serves as an important part of their medical regimen.

Administration of doxorubicin therapy is generally limited in adults and children by a cumulative dose-dependent cardiotoxicity. Irreversible cardiomyopathy with serious congestive heart failure can be a significant risk in patients who receive doses in excess of 500-550 mg/m$^2$. Unfortunately, the dose that precipitates congestive heart failure varies widely (ranging from 30-880 mg/m$^2$ in a report of 1487 patients studied over a seven year period). Those subjects with advanced age or mild reductions in left ventricular systolic function at rest (left ventricular ejection fraction [LVEF] ≤50%), are at greatest risk. In western industrialized countries, it is typically older subjects with cancer and some degree of underlying heart disease whom often are in greatest need for doxorubicin therapy, but for whom medication may be withheld due to potential cardiotoxicity.

One method for detection of doxorubicin-induced cardiomyopathy is intramyocardial biopsy with concomitant left and right ventricular pressure measurements made during cardiac catheterization. Unfortunately, this method involves an invasive procedure and may not be well suited for repetitive measurements over time. Radionuclide ventriculography is also widely used to screen those individuals at risk for developing doxorubicin-induced cardiomyopathy. Individuals who develop a reduction in LVEF of 10% or greater or those individuals who have a fall in ejection fraction to lower than 50% during treatment are at greatest risk for developing irreversible cardiotoxicity. While this information is useful as a potential screening technique, for some individuals, the drop observed in LVEF occurs too late to avert the development of irreversible cardiomyopathy. For this reason, the total dose of doxorubicin may be unduly limited for patients receiving chemotherapy. Importantly for many individuals, doxorubicin therapy is often stopped before patients derive maximal benefit of the drug regimen. A noninvasive, widely available method for accurately detecting those individuals who go on to develop cardiotoxicity would have marked clinical utility.

In the past, investigators have established the utility of MRI for identifying necrotic tissue within the left ventricle in patients sustaining myocellular injury. This technique incorporates the acquisition of gradient-echo pulse sequences with nonselective preparatory radiofrequency pulses after intravenous administration of gadolinium chelates. In regions of myocardial necrosis, heightened signal intensity occurs on images collected 20 minutes after contrast administration that corresponds to expansion of extracellular volume due to myocellular membrane disruption and increased capillary permeability. This methodology has been utilized to identify transmural myocellular necrosis in patients sustaining acute or chronic Q-wave (ST-segment elevation), and subendocardial (non-transmural) injury in patients sustaining a non-Q-wave (non ST-segment elevation) myocardial infarction. The amount of necrosis found during MRI displays an inverse relationship with recovery of systolic thickening after coronary arterial revascularization. The absence of gadolinium hyperenhancement 20 minutes after contrast administration is associated with myocardial viability and subsequent improvement in left ventricular contraction after sustaining a ST-segment or non ST-segment elevation myocardial infarction. Although some felt delayed enhancement techniques may overestimate regions of myocellular necrosis in the acute infarct, recently, a tagging study in animals indicated that delayed enhancement techniques do identify early myocellular necrosis after myocardial infarction (MI). It is believed that, in border zones of infarcts, dead cells may move due to tethering from adjacent live regions.

With MRI, cardiac structure can be imaged and LV function directly assessed with high temporal and spatial resolution. Since acoustic windows do not limit image acquisition, the utility of MRI is high particularly in subjects with a large or unusual body habitus. This heightened clarity of the images allows investigators to perform quantitative measures of LV structure and function with higher precision than that achieved with radionuclide and ultrasound techniques. A 5% change in LVEF in patients with reduced LV function can be detected with 90% power at a p-value of 0.05 with a sample size of 5 patients per group in a parallel study design. Depending upon operator experience, the same 5% change in LVEF can require an echocardiographic assessment of >100 subjects per group in the same study design. Similarly, the heightened spatial resolution (1 mm$^2$ pixel sizes) achieved with delayed enhancement MRI techniques allows for the detection of micro-infarcts that heretofore may have only been appreciated as cardiac enzymatic elevations detected in serum samples, but not visualized with radionuclide or echocardiographic techniques.

In delayed enhancement imaging, a contrast agent is administered to a patient and an image is acquired after the contrast agent has had an opportunity to be distributed to area that is to be imaged such that the contrast agent remains in injured tissue but does not remain in healthy tissue. Such delayed enhancement imaging may be used, for example, to identify myocardial infarcts, as the necrotic tissue of the infarct region will retain the contrast agent while the contrast agent will be purged from the healthy tissue. As such, the infarct may appear as a localized region of higher intensity. Conventionally, delayed enhancement imaging may be used to identify localized regions of tissue damage in tissues such as cardiac tissue, brain tissue, nerve tissue or the like.

To compare serial acquisitions of MRI images and related voxel data, alignment of the slices for the images (aligning the image slices from different acquisitions) can be important to reliably detect intensity changes in voxels in different images of a patient and/or to be able to discard less relevant neighborhoods of voxels that might skew the intensity values (and hence the analysis) of a certain region or regions of the heart or other tissue being interrogated.

SUMMARY OF THE INVENTION

Embodiments of the present invention provide images and/or visual tools useful for non-invasively evaluating cardiac injury. Some embodiments may be particularly suitable for evaluating cancer patients before, during and/or after cancer treatments, for cardiac injury associated with cancer treatments such as chemotherapy and/or radiation therapy. Some embodiments of the invention may also be particularly suitable for evaluating patients with cardiotoxicity or cardiac injury associated with and/or arising from other sources such as, for example, drugs used to treat other conditions, as well as chemical exposure (such as ingestion/inhalation of a poison or gas), environmental exposure, insect bites, snake venom, animal bites, viral, staph, or bacterial infections, as well as cardio status due to other disease states, infectious or otherwise, aging, trauma, and the like.

Embodiments of the present invention provide methods, systems and/or computer program products for providing physician interactive tools that can be used to evaluate tissue characteristics, including one or more of: cardiotoxicity-induced cardiac injury using voxel/pixel histogram data, identification of injured tissue or alteration of the ratios of native tissue components or chemical or anatomical markers, such as shifting the amounts of normal myocytes and fibrotic tissue in the heart, identifying increases in the amount of extracellular components or fluid (like edema or extracellular matrix proteins), or detecting infiltration of tumor cells or mediators of inflammation into the tissue of interest in a patient, such as a human being.

Some embodiments are directed to physician interactive workstations. The workstations can include a display with a 3-D diagnostic image of a patient's heart illustrating substantially an entire population of voxels illustrating measures of voxel intensity in color scale.

In some embodiments, the display is configured to display a plurality of voxel intensity histograms in a plurality of regions of interest in the heart, the voxel intensity histograms defining voxel data used to generate the 3-D image of the heart, the plurality of voxel intensity histograms being selectively viewable by a clinician.

In some embodiments the workstation is configured to display a CMR medical image of the patients heart, and wherein the workstation further comprises an electronic boundary-tracing tool configured to accept user input to electronically define at least one boundary of a target region of a heart in the medical image of the patient on the display.

In particular embodiments, the workstation may be configured to evaluate intensity of voxels associated with tissue within the defined boundary of the target region of the heart whereby cardiotoxicity is evaluated. The electronic boundary tracing tool configured to accept user input can be used to define a plurality of adjacent regions of interest in a left ventricle myocardium and the workstation can be configured to analyze a chemotherapeutic induced cardiotoxicity state of the patient based on intensity voxel data associated with the regions of interest.

Other embodiments are directed to cardiotoxicity evaluation signal processor circuits. The circuits can include: (a) a cardiac image generator module configured to generate a 3-D image of the population of intensity voxels of the heart in communication with a display; and (b) a histogram module in communication with the cardiac image generator module configured to generate a plurality of histograms of voxel intensity data associated with regions of interest in the heart.

In some embodiments, the circuit also includes an electronic boundary tracing tool in communication with a workstation display the electronic boundary tracing tool is configured to accept user input to electronically define a boundary of at least one target region of interest of a heart in a medical image of a patient on the display, and wherein voxel data for at least one of the histograms is associated with a region of interest based on the user defined boundary of the at least one target region of interest.

In some embodiments, the electronic boundary tracing tool is configured to accept user input to define epi and endo cardial boundaries of a left ventricle myocardium.

Other embodiments are directed to methods of evaluating cardiac images. The methods include accepting user input to electronically draw at least one boundary of a target region of interest of a left ventricle myocardium in a medical image on a display; and electronically associating voxels residing in the drawn boundary to the region of interest defined within the drawn boundary.

The method may optionally include electronically generating at least one histogram of intensity data of at least one region of interest in the left ventricle myocardium using voxel data within the boundary drawn with user input.

The method may also optionally include: electronically assigning voxel intensity data to a region of interest based on epi or endo cardial boundaries drawn by the accepting user input step and/or electronically drawing a region of interest outside the patient in the image associated with background noise.

Other methods are directed to presenting global injury data to a clinician. The methods include generating a 3-D image of a heart on a display, the image visually illustrating in color, different intensities of a population of voxels the image.

The methods can also include generating a visual 2-D compartmental model of the heart illustrating the different intensities of the population of voxels within respective compartments of the heart.

Other embodiments are directed to computer program products for evaluating cardiotoxicity in a patient. The products include a computer readable medium having computer readable program code embodied therein. The computer readable program code includes: (a) computer readable program code configured to accept user input to electronically draw a boundary line associated with at least one target region of interest in a left ventricle myocardium of a medical image of a patient on a display; (b) computer readable program code configured to generate a histogram of voxel intensity of the at least one region of interest with voxels within the region of interest defined by the drawn boundary; and (c) computer readable program code configured to generate a 3-D image of intensities of a population of voxels across the heart; and (d) computer readable program code configured to determine a likelihood of cardiac injury associated with cardiotoxicity due to chemotherapy.

Still other embodiments are directed to systems for non-invasively predicting cardiac injury due to cardiotoxicity prior to an irreversible state. The systems include: (a) a graphic user interface (GUI) in communication with a display for accepting user input to draw at least one boundary about at least one target region of interest in a left ventricle myocardium in an MRI or CT image of a patient; and (b) a signal processor circuit configured to electronically generate at least one histogram of intensities of voxels/pixels in the MRI or CT image of the at least one region of interest based on boundary data from the boundary drawn with the GUI.

The system may also be configured to electronically determine a likelihood of cardiac injury due to cardiotoxicity based on data from the at least one histogram.

Some embodiments are directed to systems for non-invasively evaluating cardiac injury due to cardiotoxicity. The systems include a signal processor circuit configured to generate a 3-D image of voxel data of a patient's heart that visually illustrates differences in intensity of voxels associated with the heart and locations and intensity of clusters of voxels with similar intensity across at least a major portion of a population of voxels obtained from a CMR or CT image of a patient's heart, wherein voxels of intensity representing cell injury and cell death are visualized.

The region of interest may include, for example, at least one of the heart or compartments or components thereof, blood, muscle, brain, nerve, skeletal, skeletal muscle, liver, kidney, lung, pancreas, endocrine, gastrointestinal and/or genitourinary tissue.

A characteristic of the region of interest of the first image and of the second image is determined so as to allow a comparison of the first image and the second image to determine a potential for a change in a tissue characteristic such as may be caused, for example, by a global injury of the tissue of the region of interest. Such a comparison may include a measure of intensity, for example, comparison of mean, average characteristics, histogram shape, such as skew and kurtosis, or distribution of intensities within the histogram.

In further embodiments of the present invention, the global characteristic is a characteristic of pixels/voxels of the region of interest that is based on substantially all of the pixels/voxels in the region of interest. The global characteristic may be an average or mean intensity of pixels/voxels in one or more sections, partitions or a region of interest. The tissue in the region of interest may be at least one of cardiac tissue, brain tissue and/or nerve tissue. The first image and the second image may be magnetic resonance imaging (MRI) images.

While certain embodiments of the present invention are described herein with reference to the detection of tissue characteristics, such as global injury in a patient, such as a human, additional embodiments of the present invention may include detection of global injury in vertebrate or invertebrate animals, reconstructed tissue and/or synthetic tissue. Accordingly, certain embodiments of the present invention should not be construed as limited to the detection of global injury in a human patient.

Particular embodiments of the present invention provide methods, systems and/or computer program products for detecting global cardiac injury in a patient using a GUI that accepts user input to draw a boundary about a target subpart of the heart.

In further embodiments of the present invention, the images are Magnetic Resonance Imaging (MRI) images and/or X-ray Computed Tomography (CT) images. Also, the measure of intensity of the first cardiac image and the measure of intensity of the second cardiac image may be average and/or mean intensity of the respective images.

As will be appreciated by those of skill in the art in light of the present disclosure, embodiments of the present invention may be provided as methods, systems and/or computer program products.

BRIEF DESCRIPTION OF THE DRAWINGS

FIGS. 29A-29C are schematic illustrations of exemplary different GUI input formats that can be used to draw or trace boundaries in a medical image according to embodiments of the present invention;

DESCRIPTION OF EMBODIMENTS OF THE INVENTION

Figure 1:
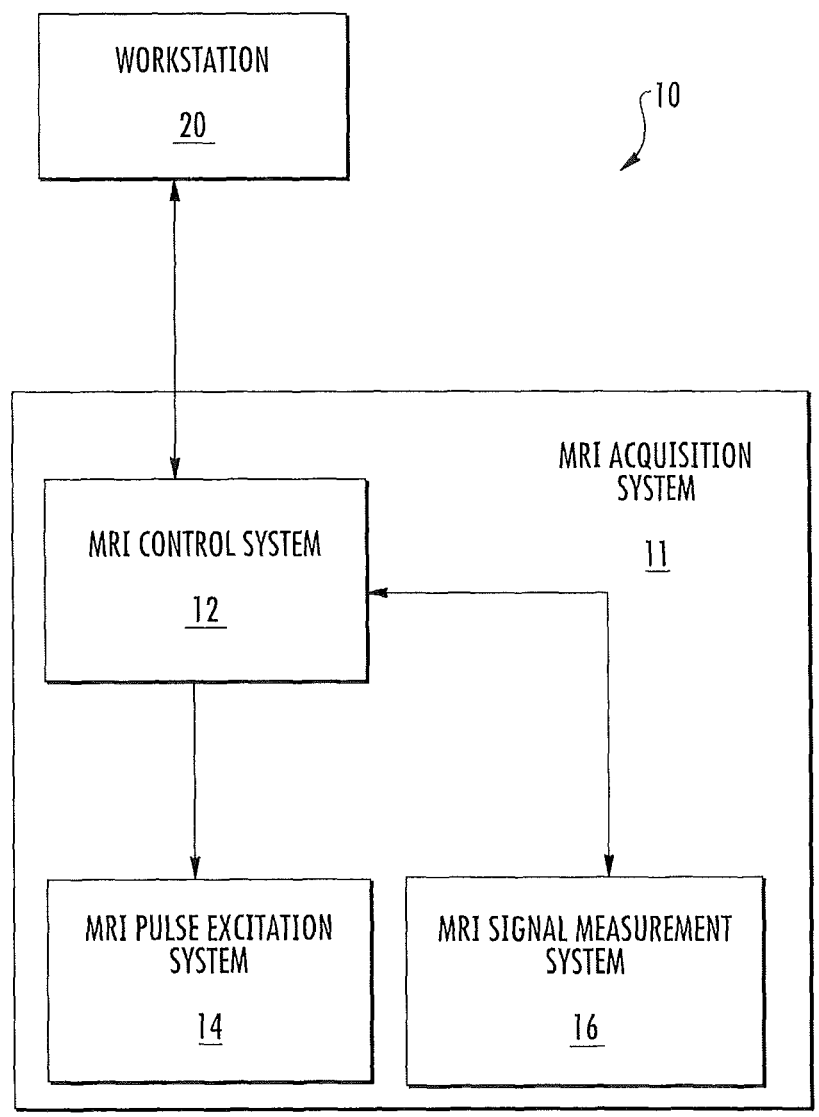
FIG. 1 is a block diagram of an MRI system according to embodiments of the present invention.

The present invention now will be described more fully hereinafter with reference to the accompanying drawings, in which embodiments of the invention are shown. However, this invention should not be construed as limited to the embodiments set forth herein. Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items. Broken lines illustrate optional features or operations unless specified otherwise. In the claims, the claimed methods are not limited to the order of any steps recited unless so stated thereat.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/ or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein. Well-known functions or constructions may not be described in detail for brevity and/or clarity.

The term "interactive" refers to a device and/or algorithm that can respond to user input to provide an output. The term "spline" refers to free-form curves defined with a set of control points. Drawing of a spline curve is by placement of these points. Generally described, each point has an associated "shape factor" which determines the approach of the curve to the point. A shape factor of −1 means the curve passes through the point (interpolation). A factor of 0 means an angular line, like an ordinary polyline. A factor of 1 means an approximated line, where the curve approaches the point but does not reach it. An open or closed spline can be selected using a spline dialog. An object or point can be moved by holding down an input key, such as <Shift>. The control points can be edited using a point editing mode where a handle to move the control point. For example, holding down <Control> and dragging on a handle to alter the shape factor of that control point.

As is known to those of skill in the art, the phrase "drawing a region of interest in air," does not literally mean "in air," but rather that the line or curve is drawn outside the body (and/or heart) in the image to obtain a corresponding background of noise data that can be used to adjust voxel intensity data.

As used herein, the term "image" refers to a spatial signal that may be evaluated to obtain a desired measure of signal intensity. The image can be visualized or displayed in 2-D what appear to be 3-D images, volume data representing features with different visual characteristics such as with differing intensity, opacity, color, texture and the like. Thus, as is well known in the art, the term "3-D" in relation to images does not require actual 3-D viewability (such as with 3-D glasses), but merely a 3-D appearance on a display.

The term "color scale" refers to using color to visually represent differences in a measure of intensity with similar colors representing similar intensities. Different intensity values can have different colors. Small differences in intensity may be indicated by a graduated scale of the same color.

The term "irreversible cardiac state" refers to a clinical change in heart function that is generally chronic (cannot self repair) that undesirably affects a patient's cardiac output or ability, whether in contractility, LVEF, pumping, rate or other quantitative measure.

The term "chemotherapy" and derivatives thereof refer to therapeutic medicaments, pharmaceuticals or other treatments used to treat a patient. Examples of chemotherapy agents include, but are not limited to, targeted antigens, antibodies, antineoplastics such as alkylating agents, nitrogen mustards, nitrosureas, antibiotics, hormonal antagonists or androgens, antiandrogens, antiestrogens, estrogen/nitrogen mixtures, estrogens, gonadotroopin releasing hormones, immunomodulators, and other appropriate therapeutic agents. Examples of marker or expression-based evaluation of antigens/antibodies include those used in cancer evaluation and/or treatment. Examples of tumor-associated antigens of interest may include the CD-20 antigen (on B lymphocytes) for which treatment may include agents having antibodies to the CD-20 antigen and human epidermal growth factor (HER2) associated with some breast tumors. It is noted that HERCEPTIN® is currently approved for breast cancer treatment. It is contemplated that other biomaterials may also be suitable to as chemotherapeutic agents, including, but not limited to, mixed cultures containing tumor cells and blood-derived lymphocytes (which may be from the patient) to produce cytolytic T lymphocytes (CTL) (or CTL clones or autologous CTL), that lyse the autologous tumor cells (which may be used in connection with melanoma, renal, bladder, head and neck carcinomas, non-small lung cancer, and the like). Other potential antigens/antibodies of interest include MAGE-1, MAGE-3, BAGE, GAGE-1, and GAGE-3. See, e.g., UCL Christian de Duve Institute of Cellular Pathology, *Ludwig Institute For Cancer Research*, URL www. lcp.u-cl.ac.be/report95/licr95.html.

As will be appreciated by one of skill in the art, the present invention may be embodied as methods, systems, or computer program products. Accordingly, the present invention may take the form of an entirely hardware embodiment, an entirely software embodiment or an embodiment combining software and hardware aspects all generally referred to herein as a "circuit" or "module." Furthermore, the present invention may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present invention may be written in an object oriented programming language such as Java®, Smalltalk or C++. However, the computer program code for carrying out operations of the present invention may also be written in conventional procedural programming languages, such as the "C" programming language. The program code may execute entirely on a user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider). Furthermore, the user's computer, the remote computer, or both, may be integrated into other systems, such as an MRI system and/or X-Ray Computed Tomography system.

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

MRI procedures are well established for identifying myocellular injury and LVEF in patients with ischemic cardiomyopathy secondary to coronary arteriosclerosis. Such procedures may identify localized cardiac injury. However, it is believed that such non-invasive imaging has not been utilized to identify global cardiac injury in patients with cardiomyopathy secondary to chemotherapy administration. Early detection of myocellular injury could offer an opportunity to adjust medication dosages and reduce and/or minimize the cardio-toxic effects associated with chemotherapy. In this manner, maximal doses of chemotherapy could be administered to patients in the absence of myocellular injury and the desired effect of the chemotherapy medications may be more fully realized. While embodiments of the present invention may be particularly useful in doxorubicin therapy, embodiments of the present invention may also be utilized in evaluating patients undergoing other chemical therapies and/or radiation therapy. Embodiments of the invention may be useful for evaluating global cardiac status in drug discovery programs, clinical trials and/or diagnostic environments using data from the detection of global cardiac injury.

Thus, it will be appreciated that although described herein primarily with respect to cardiotoxicity induced by chemotherapy and/or radiation, the evaluation techniques described herein can be used for other medical evaluations of cardiac injury and/or cardiotoxicity for other conditions, injuries or other toxic exposures. For example, embodiments of the present invention can evaluate cardiotoxicity associated with one or more of chemical or environmental toxin exposure (airborne, water, waste, and the like), poison (including chemical and/or insect, snake or other venoms), prescription or non-prescription drugs (such as those not associated with cancer), disease states, aging, viral, staph and bacterial infections, trauma and the like.

Embodiments of the present invention provide for detection of a change in tissue characteristics, such as may result from an injury utilizing a comparison of a global characteristic of a region of interest in an image of the region of interest. A global characteristic of a region of interest is a characteristic of the region of interest that is based on one or more characteristics of all or substantially all of the pixels/voxels of the region of interest. Thus, in certain embodiments of the present invention, the global characteristic may be substantially independent of the location of pixels within the region of interest. Examples of a global characteristic may include but are not limited to a statistical analysis of a characteristic of pixels/voxels in the region of interest such as average intensity, a histogram of intensity values or other statistical analysis. The use of a comparison of global characteristics of images may allow for detection of injury where the pattern of injury is random and/or is not detectable at the resolution of the images that are compared. Embodiments of the present invention may also use global characteristics, not only to detect injury to an area, but also to detect abnormal accumulation of materials that are not found in their normal ratios within native tissue.

Embodiments of the present invention may also be used with molecular imaging strategies: for example, directing the contrast with molecular recognition sites to areas of tissue and quantifying the presence of a target or molecular process. Thus, particular embodiments of the present invention may have application in detecting cancer, inflammation, infection, swelling or edema, scar tissue, etc. Also, embodiments of the present invention could be used to define metabolic pathways that are functioning within tissue in an organ system. Particular embodiments of the present invention provide for the detection of global cardiac injury utilizing non-invasive imaging before and/or after administration of a contrast agent and/or in connection to exposure to a toxin, such as, for example, a chemotherapeutic agent.

Non-invasive imaging techniques suitable for use in embodiments of the present invention include Magnetic Resonance Imaging (MRI), ultrasound, X-ray Computed Tomography (CT), single photon emission computed tomography (SPECT) and/or positron emission tomography (PET).

In some embodiments, comparisons may be made between a first or baseline image and a second image and the contrast of the image analyzed to detect the presence of global cardiac injury.

In some embodiments, at least one histogram of intensity of voxels of cardiac tissue from an image of a patient can be used to assess cardiotoxicity-induced cardiac injury. Typically, the image-based histogram data includes voxels of at least the left ventricle myocardium, where cardiac injury can be associated with reduced cardiac function, such as a decrement in LVEF that may result in a quality of life issue or a reduction in patient activity. Classification of the histogram data as being likely to result in cardiac injury can be based on norms of a population (or population segment, such as age, race, gender, etc.) or a statistical model of probability of cardiac injury based on histogram data, such as a substantial decrement in LVEF (typically a decrease of greater than about 10% or a reduction below a threshold value of 50% in a baseline image) associated with a high (and/or increased) value of intensity and/or a histogram shape, lineshape or voxel intensity distribution pattern.

In particular embodiments, a tail portion of the histogram of mean intensity voxels of an MRI or CT image of a left ventricle myocardium may include particularly predictive data that can be used to establish the probability of undesirable decrement in LVEF. One or more additional correlative factors may also be considered in a statistical correlation model, such as, but not limited to, left ventricle volume, mass, a patient's weight, age, gender, race, chemotherapeutic agent (s), chemotherapeutic dose and the like.

The term "characterizing portion" means that the portion is statistically validated to be predictive of the presence of or a likelihood of developing a disease, injury or impairment. The term "tail portion" refers to a portion of a histogram of percentage (x-axis) versus intensity (y-axis) that is to the left of center or a peak (typically associated with higher intensity values) of the curve or shape. The tail portion may include at least one of a $1\sigma$, $2\sigma$, $3\sigma$, $4\sigma$, $5\sigma$ and/or $6\sigma$ portion of the intensity distribution of the curve associated with a voxel intensity histogram. Typically, the tail portion is a subset of the entire tail and may include only the portion representing a $2\sigma$, $3\sigma$ and/or $4\sigma$, or a $2\sigma$ and/or $3\sigma$ portion of the data. The tail portion can be another portion of the curve or shape if a different histogram construct is used. For example, if the intensity is on the x-axis and the percentage is on the y-axis, the characterizing portion of the curve may change using the same data.

The term "signature" means a defined recognizable (visually, optically or electronically recognizable) shape or pattern statistically correlated to be predictive of an actual or likelihood of developing a disease, injury or impairment, typically of the heart.

In some embodiments, a histogram or histograms taken at one or more points in time can be used to evaluate cardiotoxicity to determine a probability of increasing cardiac injury, before irreversible injury to the LVEF occurs. Such a probability of occurrence can be used to alter a planned chemotherapeutic dose, a change in the chemotherapeutic drug, and/or timing of administration of a chemotherapeutic dose.

As used herein, the term "global injury" refers to a change in tissue composition and/or function that is in a substantially randomly distributed pattern and/or in a pattern that is not detectable at the resolution of the images that are analyzed to detect the injury. Thus, for example, "global cardiac injury" may refer to cardiac injury and/or replacement of native myocardial tissue with fibrous tissue, such as scar tissue, that results in necrosis and/or fibrosis in a substantially randomly distributed pattern and/or in a pattern that is not detectable at the resolution of the images that are analyzed to detect the injury. Global cardiac injury that may be detected by intensity analysis according to embodiments of the present invention may include, for example, viral cardiomyopathy, alcoholic cardiomyopathy, postpartum cardiomyopathy and/or idiopathic dilated cardiomyopathy. A global injury may also include disproportionate amounts of other abnormalities such as edema (extra fluid), fibrosis (scar tissue), etc. Thus, embodiments of the present invention may provide for the detection of global abnormal tissue.

Contrast agents suitable for use in embodiments of the present invention may include paramagnetic lanthanide chelates and/or paramagnetic lanthanide linked to a macromolecule, such as gadolinium DPTA. Other examples of MR contrast for perfusion imaging include the application of susceptibility agents containing iron oxide or dysprosium that introduce local inhomogeneity into the magnetic field by causing large fluctuations in the magnetic moment between blood and intracellular compartments. Imaging after the introduction of other drugs that induce cardiomyopathy, such as cocaine and/or alcohol could also be performed. These fluctuations result in the shortening of T2-star of neighboring hydrogen nuclei leading to loss of signal intensity. It is contemplated that hyperpolarized contrast agents (such as hyperpolarized noble gas or carbon solutions) may also be used, particularly ones configured to be injected as solutions.

In particular embodiments of the present invention, the same contrast agent is utilized for each image.

Additionally, certain embodiments of the present invention may provide for contrast/intensity analysis without the administration of a contrast agent. For example, another example of perfusion imaging is the assessment of myocardial perfusion or injury without the administration of a contrast agent using a blood oxygen level dependent (BOLD) cardiac imaging via a T2-prepared true FISP, or 3D-T2-weighted sequence strategy. Other techniques use endogenous contrast including spin labeling and magnetization transfer contrast. Thus, in certain embodiments of the present invention, a global characteristic of a region of interest may be detected without the administration of a contrast agent.

An exemplary system 10 according to embodiments of the present invention is illustrated in FIG. 1. As seen in FIG. 1, an intensity analysis/MRI system 10 includes an MRI acquisition system 11 that may include an MRI control system circuit 12, an MRI pulse excitation system circuit 14 and an MRI signal measurement system circuit 16. The MRI control system circuit 12 controls operations of the MRI acquisition system 11 to obtain and provide MRI images during a cardiac cycle or portions thereof of a patient. The MRI control system circuit 12 may also assemble and transmit the acquired images to a workstation 20 or other such data processing system for further analysis and/or display. The workstation 20 may be, in an MRI suite or may be remote from the MRI suite. The MRI pulse excitation system circuit 14 and the MRI signal measurement system circuit 16 are controlled to acquire MRI signals that may provide MRI images of the heart of a patient.

Conventional MRI systems, such as those provided by General Electric Medical Systems, Siemens, Philips, Varian, Bruker, Marconi, Hitachi and Toshiba may be utilized to provide the desired MRI image frames (typically collected after administration of a contrast agent). The MRI systems can be any suitable magnetic field strength, such as, for example, about 1.5 T, and may be higher field systems of between about 2.0 T-10.0 T.

While an exemplary intensity analysis/MRI system is illustrated in FIG. 1 and described herein with a particular division of functions and/or operations, as will be appreciated by those of skill in the art, other divisions of functions and/or operations may be utilized while still benefiting from the teachings of the present invention. For example, the MRI control system circuit 12 could be combined with either the MRI pulse excitation system circuit 14 or the MRI signal measurement system circuit 16. Thus, the present invention should not be construed as limited to a particular architecture or division of MRI functions/operations but is intended to cover any architecture or division of functions/operations capable of carrying out the operations described herein.

Figure 2:
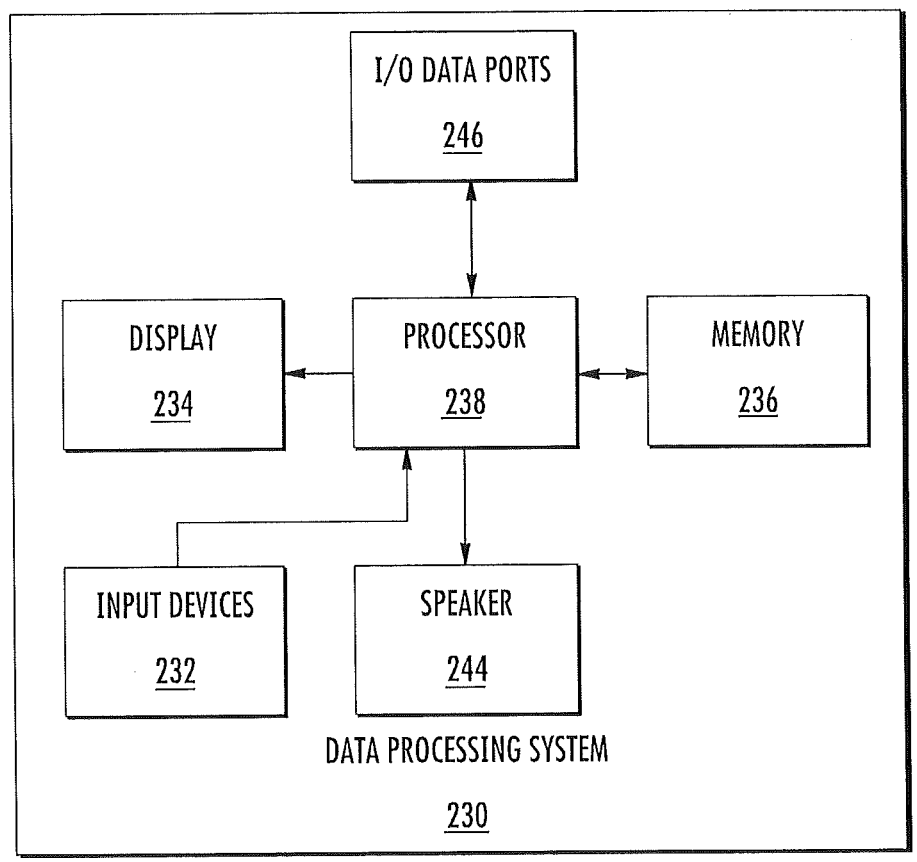
FIG. 2 is a block diagram of a data processing system according to embodiments of the present invention.

FIG. 2 illustrates an exemplary embodiment of a data processing system 230 suitable for providing a workstation 20 and/or MRI control system circuit 12 in accordance with embodiments of the present invention. The data processing system 230 typically includes input device(s) 232 such as a keyboard or keypad, a display 234, and a memory 236 that communicate with a processor 238. The data processing system 230 may further include a speaker 244, and an I/O data port(s) 246 that also communicate with the processor 238. The I/O data ports 246 can be used to transfer information between the data processing system 230 and another computer system or a network. These components may be conventional components such as those used in many conventional data processing systems that may be configured to operate as described herein.

Figure 3:
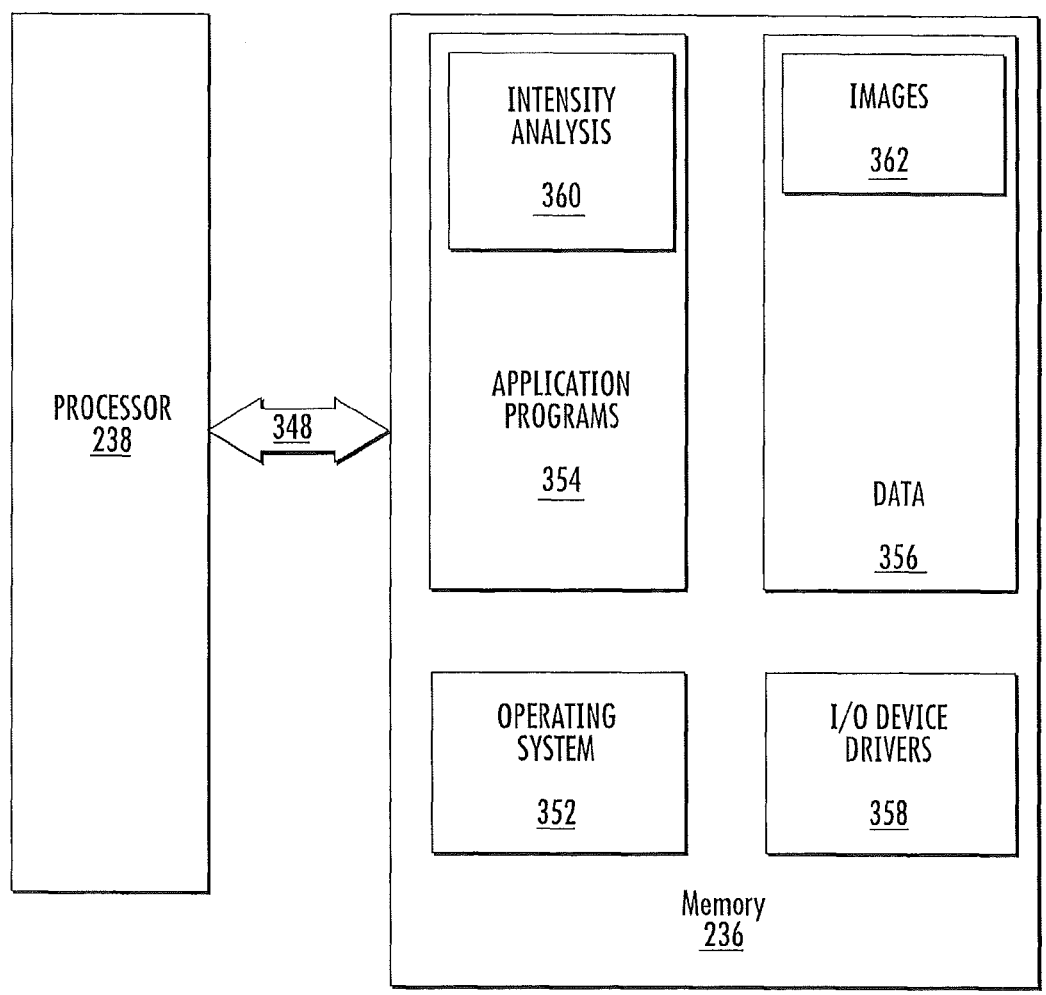
FIG. 3 is a block diagram of a data processing system according to embodiments of the present invention.

FIG. 3 is a block diagram of embodiments of data processing systems that illustrates systems, methods, and computer program products in accordance with embodiments of the present invention. The processor 238 communicates with the memory 236 via an address/data bus 348. The processor 238 can be any commercially available or custom microprocessor. The memory 236 is representative of the overall hierarchy of memory devices containing the software and data used to implement the functionality of the data processing system 230. The memory 236 can include, but is not limited to, the following types of devices: cache, ROM, PROM, EPROM, EEPROM, flash memory, SRAM, and DRAM.

As shown in FIG. 3, the memory 236 may include several categories of software and/or data used in the data processing system 230: the operating system 352; the application programs 354; the input/output (I/O) device drivers 358; and the data 356. As will be appreciated by those of skill in the art, the operating system 352 may be any operating system suitable for use with a data processing system, such as OS/2, AIX or System390 from International Business Machines Corporation, Armonk, N.Y., Windows95, Windows98, Windows2000, WindowsNT or WindowsXP from Microsoft Corporation, Redmond, Wash., Unix or Linux. The operating systems may be configured to support a TCP/IP-based or other such network communication protocol connection. The I/O device drivers 358 typically include software routines accessed through the operating system 352 by the application programs 354 to communicate with devices such as the I/O data port(s) 246 and certain memory 236 components. The application programs 354 are illustrative of the programs that implement the various features of the data processing system 230 and preferably include at least one application that supports operations according to embodiments of the present invention. Finally, the data 356 represents the static and dynamic data used by the application programs 354, the operating system 352, the I/O device drivers 358, and other software programs that may reside in the memory 236.

As is further seen in FIG. 3, the application programs 354 may include an intensity analysis application 360. The intensity analysis application 360 may carry out the operations described herein for evaluating images to detect changes in intensity that may be associated with global cardiac injury. The data portion 356 of memory 236, as shown in the embodiments of FIG. 3, may include image data 362, such as MRI image data that includes first and second images of tissue of a region of interest for comparison.

While the present invention is illustrated, for example, with reference to the intensity analysis application 360 being an application program in FIG. 3, as will be appreciated by those of skill in the art, other configurations may also be utilized while still benefiting from the teachings of the present invention. For example, the intensity analysis application 360 may also be incorporated into the operating system 352, the I/O device drivers 358 or other such logical division of the data processing system 230. Thus, the present invention should not be construed as limited to the configuration of FIG. 3 but is intended to encompass any configuration capable of carrying out the operations described herein.

Figure 4A:
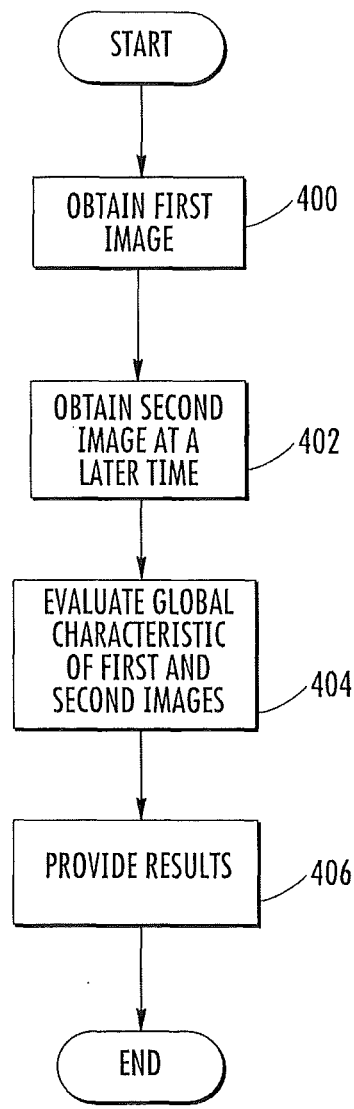
FIGS. 4A and 4B are flow charts illustrating operations according to certain embodiments of the present invention.

FIG. 4A illustrates operations according to particular embodiments of the present invention. As seen in FIG. 4A, a first image of a region of interest of tissue of a patient is obtained (block 400). An image may be obtained, for example, by acquisition of the image from an imaging system, such as the imaging systems discussed above, and/or by obtaining the image from a database, file or other storage of the image data. For example, a patient's images may be maintained in a historical database for subsequent recall as a first image for comparison. The region of interest of tissue in a patient that is imaged may, for example, include heart, blood, muscle, brain, nerve, skeletal, skeletal muscle, liver, kidney, lung, pancreatic, endocrine, gastrointestinal and/or genitourinary tissue. In particular embodiments of the present invention, the tissue may be human tissue. In other embodiments, the tissue may be animal tissue.

As is further illustrated in FIG. 4A, a second image of the tissue in the region of interest for comparison to the first image is obtained after a period of time, such as hours, days, weeks, months or even years (block 402). The second image for comparison reflects any change in the characteristics of the tissue in the region of interest. The second, comparison image may be acquired and registered (taken at the same slice locations) with the corresponding first image. The second image may also be obtained as described above with reference to the first image. Thus, for example, comparison images may be historical images as well as recently acquired images.

The first image and the second image are evaluated to determine one or more global characteristics of the images (block 404). The global characteristic of the images may, for example, be an average intensity of pixels/voxels in the region of interest. The global characteristic could also be a statistical analysis of the pixels/voxels in the region of interest. For example, the standard deviation, mean value or other statistical analysis of the pixels/voxels in the region of interest could be determined. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

The results of this evaluation are provided to a user or may be provided for further analysis (block 406). For example, a comparison of the first image and the second image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface The results of the evaluation of the global characteristic of the image of the tissue in the region of interest may be utilized in the detection, perhaps the early detection, of change in tissue characteristics such as may result, for example, from injury to the tissue or other conditions as discussed above. Such a global characteristic evaluation may be suitable in detecting tissue characteristics that result in a random pattern of different tissue characteristics in the region of interest or that are imaged at a resolution where a pattern of the tissue characteristic cannot be detected.

Figure 4B:
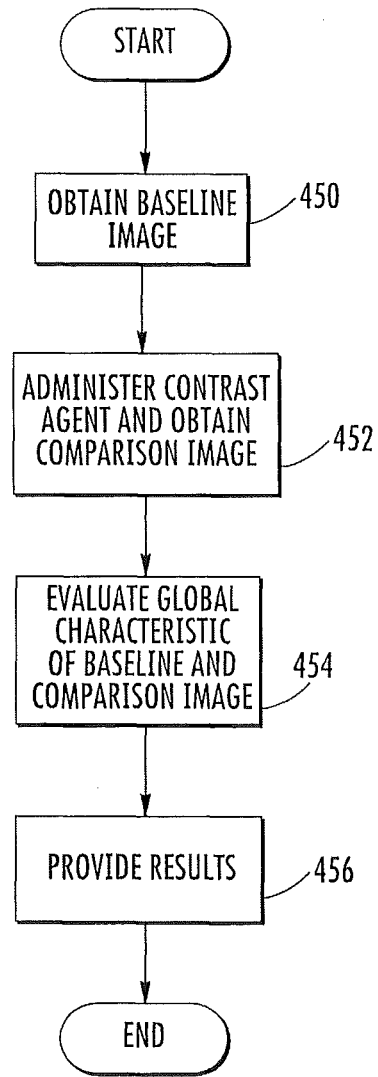

FIG. 4B illustrates operations according to particular embodiments of the present invention utilizing administration of a contrast agent. As seen in FIG. 4B, a baseline image of a region of interest of tissue of a patient is obtained (block 450). An image may be obtained, for example, by acquisition of the image from an imaging system, such as the MRI system illustrated in FIG. 1, and/or by obtaining the image from a database, file or other storage of the image data. For example, a patient's images may be maintained in a historical database for subsequent recall as a baseline image for comparison. The baseline image may be an image taken without administration of a contrast agent, after administration of a contrast agent and/or a period of time, such as twenty minutes, after administration of the contrast agent. The region of interest of tissue in a patient that is imaged may, for example, include heart, blood, muscle, brain, nerve, skeletal, skeletal muscle, liver, kidney, lung, pancreatic, endocrine, gastrointestinal and/or genitourinary tissue. In particular embodiments of the present invention, the tissue may be human tissue. In other embodiments, the tissue may be animal tissue.

As is further illustrated in FIG. 4B, an image of the tissue in the region of interest for comparison to the baseline image is obtained after administration of a contrast agent (block 452). The image for comparison reflects the effect of the contrast agent on the tissue in the region of interest. In particular embodiments of the present invention, the image may be a myocardial delayed enhancement (MDE) image. The comparison image may be acquired and registered (taken at the same slice locations) with the corresponding baseline image. The comparison image may also be obtained as described above with reference to the baseline image. Thus, for example, comparison images may be historical images as well as recently acquired images.

The baseline image and the comparison image are evaluated to determine one or more global characteristics of the images (block 454). The global characteristic of the images may, for example, be an average intensity of pixels/voxels in the region of interest. The global characteristic could also be a statistical analysis of the pixels/voxels in the region of interest. For example, the standard deviation, mean value or other statistical analysis of the pixels/voxels in the region of interest could be determined. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

For example, the global characteristic can be the standard deviation, comparison of mean, average characteristics, histogram shape, such as skew and kurtosis, or distribution of intensities within the histogram, other moment of analysis, or other statistical analysis of the pixels/voxels in the region of interest. Also, a histogram of a characteristic of the pixels/voxels in the region of interest could be provided as a global characteristic. The characteristic of the pixels/voxels that is evaluated to provide the global characteristic may include intensity, color, saturation and/or other characteristics of individual pixels/voxels as well as relative characteristics of multiple pixels/voxels, such as contrast ratios or the like.

In some particular embodiments, one of equations (1)-(3) may be used to evaluate voxel data. The standard deviation (spread of the distribution) may be defined by mathematical equation (1).

$$s = \sqrt{\frac{1}{n-1} \sum_{i=1}^{n} (x_i - \bar{x})^2} \qquad \text{Equation 1}$$

where "n" is the number of voxels measured for one individual, $x_i$ is the individual intensity of voxel i, and $\bar{x}$ is the mean of the voxels.

The skewness of the distribution, which measures the symmetry of the distribution, can be defined by equation (2).

$$\frac{\sum_{i=1}^{n} \frac{(x_i - \bar{x})^3}{s^3}}{n} \quad \text{Equation 2}$$

where n, $x_i$ and $\bar{x}$ are as defined above for equation (1) and s is the standard deviation of the distribution of voxels as defined above.

The kurtosis of distribution is a measure that describes the "tails of the distribution" and may also be known as the "peakedness" of a distribution. The kurtosis can be defined by equation (3).

$$\frac{\sum_{i=1}^{n} \frac{(x_i - \bar{x})^4}{s^4}}{n} - 3 \quad \text{Equation 3}$$

where n, s, $x_i$ and $\bar{x}$ are as defined above. If data were normally distributed the skewness and kurtosis, as defined above, both would be zero (which is not the typical situation for cardiac toxicity or injury).

The results of this evaluation are provided to a user or may be provided for further analysis (block 456). For example, a comparison of the baseline image and the comparison image may be performed and a difference in average intensity may be provided as results to a user. Furthermore, a histogram of the characteristic and/or differences in the characteristic between the baseline and comparison images may be determined and provided as a result. Additionally, the histogram could be pattern matched to a library of histogram profiles that are characteristic of particular injuries, diseases and/or conditions. The results of the determination may, for example, be provided as part of a graphic user interface The results of the evaluation of the global characteristic of the image of the tissue in the region of interest may be utilized in the detection, perhaps the early detection, of injury to the tissue. Such detection may be provided for injuries that result in a different concentration of contrast agent being present in injured versus healthy tissue. Such a global characteristic evaluation may be suitable in detecting injuries that result in a random pattern of injured tissue in the region of interest or that are imaged at a resolution where a pattern of the injured tissue cannot be detected. Thus, for example, with a 1.5 Tesla MRI imaging system, a typical myocardial infarct would not be considered a global image and the detection and location of increased intensity in an image in the location of the infarct would not be considered a random pattern of injured tissue or a pattern of injured tissue that could not be detected at the resolution of the MRI imaging system.

Figure 5:
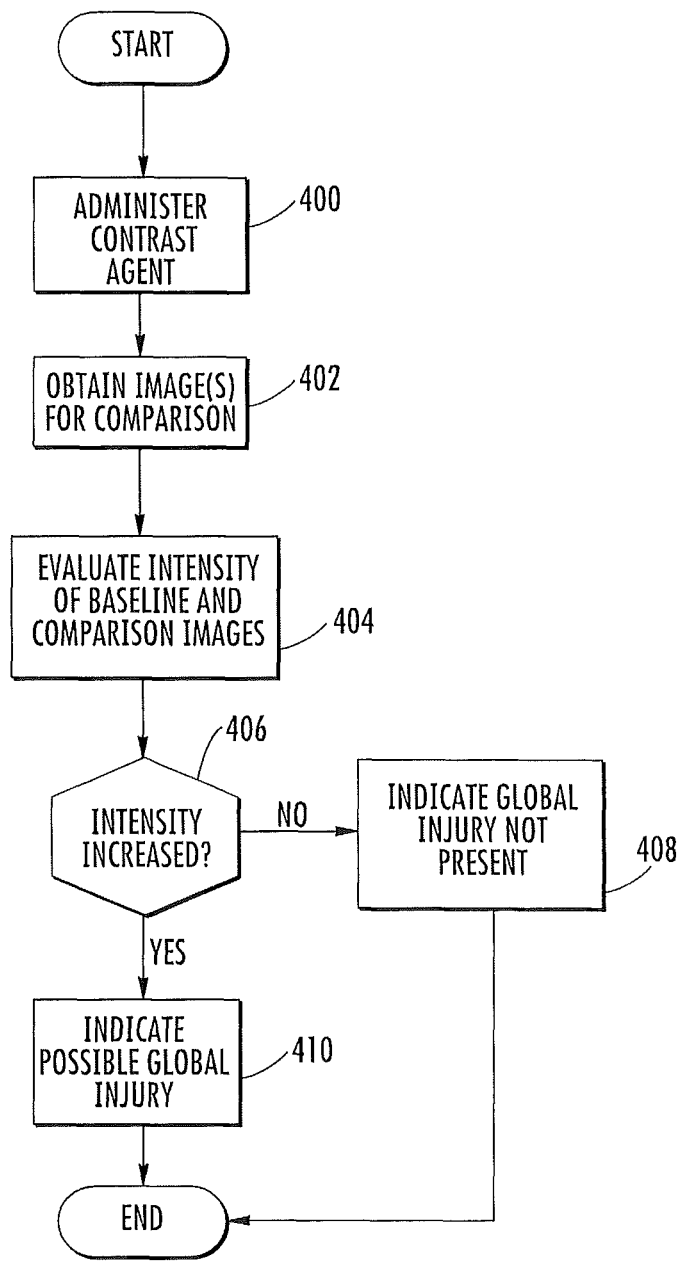
FIG. 5 is a flow chart illustrating operations according to certain embodiments of the present invention.

FIG. 5 illustrates operations according to particular embodiments of the present invention. As seen in FIG. 5, a contrast agent is administered to a patient (block 400) and an image of at least a portion of the patient's heart is acquired (block 402). In particular embodiments of the present invention, the acquired perfusion image may be a myocardial delayed enhancement (MDE) image. In MDE, after about 20 minutes after a contrast agent, such as gadolinium DPTA, is administered, ordinarily some of it has leaked into necrotic (dead) tissue and will appear bright (hence, delayed enhancement). These images may be acquired and registered (taken at the same slice locations and/or processed to align at the same locations) with the corresponding baseline perfusion images.

The acquired image is evaluated and the intensity of the image is compared to a baseline image (block 404). The baseline image is an image of the patient's heart and may be a previously acquired image that was also acquired after administration of a contrast agent. The baseline image may have been acquired prior to administration of a treatment regimen or may be an image acquired at an earlier evaluation. The comparison of images may be a comparison of average intensity and/or mean intensity of the images as discussed in more detail below. If the intensity of the image has not increased in comparison to the baseline image (block 406), then an indication that a global cardiac injury is not present may be provided (block 408). If the intensity of the image has increased in comparison to the baseline image (block 406), then an indication that a global cardiac injury may be present may be provided (block 410).

In still further embodiments of the present invention, the evaluation of global image characteristics, such as the intensity of the cardiac images, may be performed automatically or partially automatically utilizing image processing techniques. An automatic comparison may, for example, also include registration of the differing images to each other. Such a registration may be provided utilizing conventional pattern recognition and/or alignment techniques such that corresponding pixels of the images or portions of the images are each associated with approximately the same physical location within the patient.

In particular embodiments, registration may be across the entire left ventricle myocardium using a plurality of slices, such as at least about three, typically at least about eight, and more typically about 10, short axis slices per patient. Co-registration may be calculated as the union of left ventricle voxel locations which may be carried out to provide at least about a 95% overlap of regions between images.

In particular embodiments of the present invention, a patient may be taken to the MRI suite where he/she will be placed supine on the MRI table and ECG leads and respiratory gating bellows applied. MRI scans may be performed on, for example, a 1.5 Tesla GE $CV_i$ scanner with a phased array surface coil applied around the chest to optimize signal to noise ratio, or another MRI scanner. Images may be acquired using a fast gradient echo technique, with the repetition time (TR) and echo time (TE) based on the R-R interval of the subject. Multislice coronal, gradient echo sequences may be used to obtain scout images of the chest and locate the left ventricle. Subjects may be injected intravenously with a gadolinium contrast agent (0.2 mmole/kg Gadoteridol (Prohance, Bracco Diagnostics, Princeton, N.J.)). The time of this injection may be recorded.

After locating the left ventricle, a series of steady state free precession, short axis views can be acquired perpendicular to the left ventricle covering from the base to the apex. Imaging parameters can be, for example, 32 cm field of view, 35 degree flip angle, 8 mm slice thickness, 2 mm inter-slice space, and a 256×128 matrix. The scans may have a temporal resolution of about 40 msec to identify end systole for determinations of LV volumes, EF (ejection fraction) and mass using known protocols. See, Natori et al., *Cardiac MR Imaging in MESA: Protocol and Normal Values*, AM J Roentgenol (In Press) (describing a multi-center cohort study such as the Mutli-Ethic Study of Atherosclerosis with greater than 6000 subjects). For example, to measure LV volumes, a series of LV short axis views spanning the base to the apex of the heart can be acquired. The volume is determined by summing the endocardial area within each slice multiplied by the slice thickness. Endocardial area in each segment can be calculated at end-diastole and end systole. This technique is known as Simpson's rule technique and can calculate volumes without using formulas with assumptions about LV shape. Left ventricular ejection fraction can be calculated using the relationship: (end-diastolic volume-end-systolic volume)/end-diastolic volume. See Semelka et al: *Interstudy reproducibility of dimensional and functional measurements between cine magnetic resonance studies in the morphology abnormal left ventricle*, Am. Heart J. 119:1367-1373 (1990).

About twenty minutes from the time of the contrast injection, at least three short axis views in the same slice positions as the LV volume determinations, such as (basal, middle, and apical) delayed enhancement images, may be acquired using a fast gradient echo preceded by a nonselective saturation pulse. Landmarks for these acquisitions may be measured from the coronary sinus within the atrio-ventricular groove extending horizontally across the mitral valve annulus. These images may be acquired using a 38 cm field of view, 24 views per segment, 8 mm slice thickness (2 mm gap), 2 NEX, 256×256 imaging matrix, and a 0.75 rectangular field of view. The inversion time (TI) for the delayed enhancement images may be adjusted 140 to 160 msec to provide a uniform dark background. Additionally, in these three short axis slice positions, a fast-gradient-recalled echo pulse sequence may be used with phase-encode ordering. These images may be subjected to phase-sensitive reconstruction that reduces the variation in apparent contrast intensity that is observed in the magnitude images as TI is changed. In addition, the phase-sensitive reconstruction may decrease the sensitivity to changes in tissue $T_1$ with increasing delay from the gadolinium contrast injection.

Upon completion of the image acquisition, the locations, measurements, and representative images may be transferred electronically to a database. This information may be available to the MRI technologist via a PC workstation at the time of each scan and facilitate the relocation of slice positions (registration) on subsequent studies.

Figure 12:
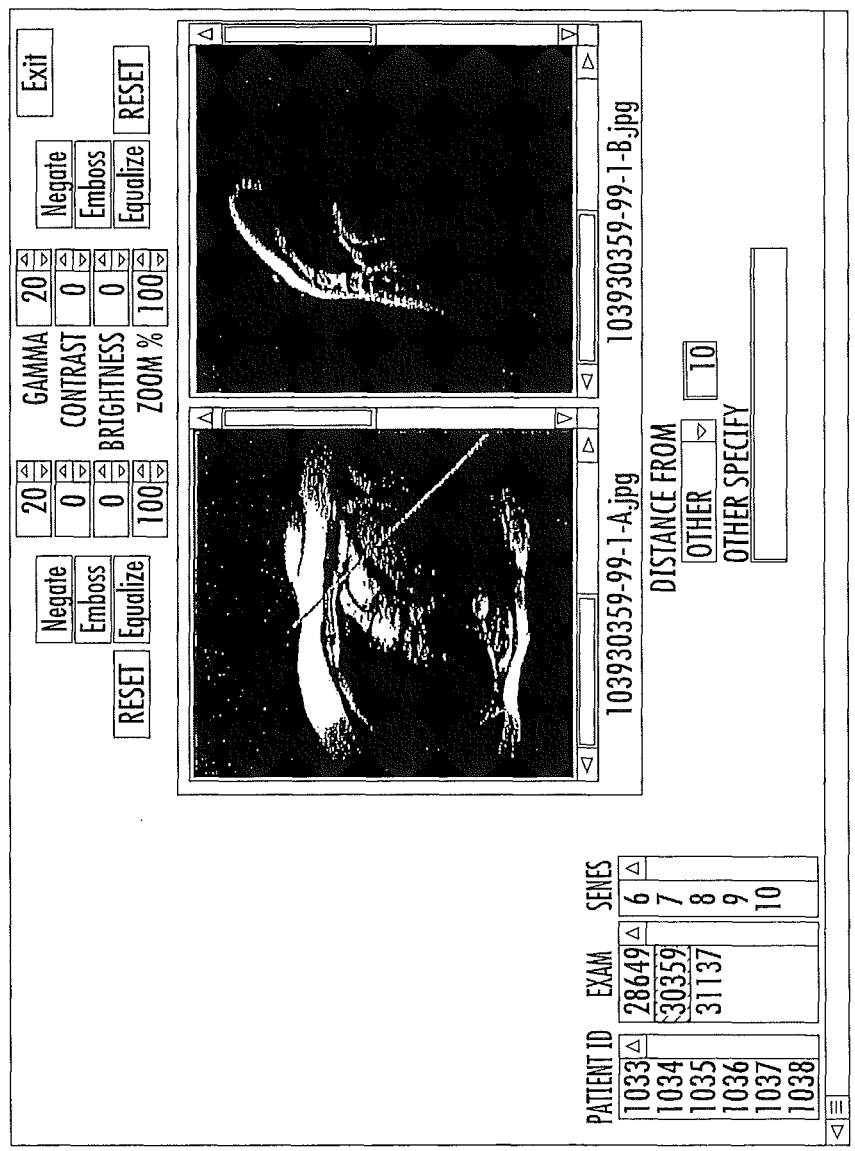
FIG. 12 is a screen capture of image planning software for reproducing slice positions.

FIG. 12 illustrates a screen capture of software for planning image slices. Such software may provide electronic copies of image planning slices and positioning coordinates that are saved for retrieval during subsequent visits in a study. This has the effect of improving the ability of the MRI technologist to reproduce slice positions from the previous visits. In the example of FIG. 12, a long-axis view of the heart with a resultant delayed enhancement short axis view is shown.

On the delayed enhancement acquisitions, regions of interest (ROIs) encompassing the LV myocardium on all of the multi-slice acquisitions may be determined. High signal intensities associated with the blood pool within the LV cavity may be avoided. The signal intensity and location (x, y, and z coordinates) of each (or selected) voxel within the ROIs may be recorded from both baseline and delayed enhancement images. Values may also be derived from subtracting the mean intensity for a separate ROI, for example, without contrast agent, from the intensities by using a separate ROI within the air/space outside of the body. The ROIs may be utilized as discussed below in the Examples in determining a change in intensity between two images.

In some embodiments, a slice position between first and second acquisitions (or more) can be aligned using physician interactive tools that can allow the physician to draw freehand or with software-guidance (i.e, GUI tools such as adjustable size/shape curves), the endo- and epi-cardial boundaries of the LV myocardium and can also allow a physician to define a region of interest for the background noise in the air as discussed above. The defined LV boundaries can help avoid high signal intensity voxels located beyond the LV myocardium. This background ROI can be automatically sized to have the same area (hence the same number of voxels) as the annular LV ROI. This may facilitate proper scaling for the subtraction of the air histogram from the LV histogram in the noise removal process. Histograms of the voxel intensities in the LV or air regions, as well as a difference histogram, can be plotted using automated software algorithms with customization options. A 3-D image of the heart illustrating the different voxel intensities may be generated; such an image differs from conventional CMR images in that voxel intensities are quantified (relatively or absolutely) and visually indicated on the image with similar intensities having similar grayscale or color (such as with different and graduated shades of color for different voxel intensities) to emphasize the distribution on injured or dead cells over the heart and/or target compartments of the heart. Thus, the heart can be illustrated "lit-up" with visually accentuated regions of impaired or dead cells for ease of viewability and reference for a clinician.

In some embodiments, other known noise or background removal strategies can be employed, such as, for example, Wiener and Kalman filtering, that can consider the location of noise voxels removed from the image. See Gonzalez et al., *Digital Image Processing*, Addison-Wesley Pub. Co., p. 279 (1992).

Figure 13:
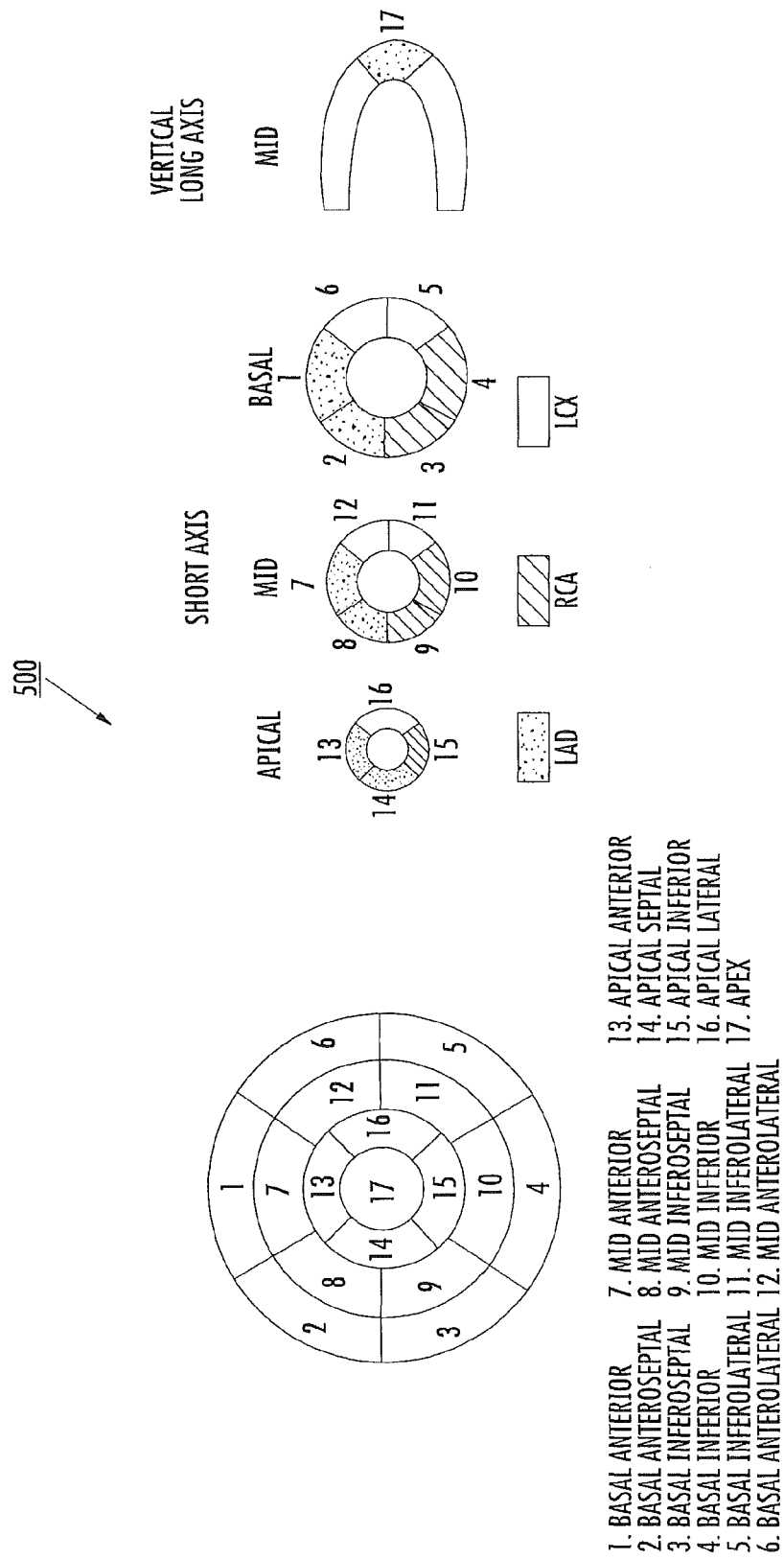
FIG. 13 is a schematic illustration of a standardized compartmental heart model.

In some embodiments, a standardized model of the heart 500 can be visually generated with the voxel intensity data such as shown in FIG. 13. The model shown in FIG. 13 is a 17-segment model of the heart that can visually illustrate cardiac status to a clinician. This model corresponds to the model developed by the American Heart Association and the American College of Cardiology to standardize reporting of radionuclide scintigraphy, echocardiography, Computed Tomography and MRI data related to LV myocardial function, perfusion and injury. As shown, regional blood flow to the compartments or segments in the model can be ascribed to the left anterior descending anterior (LAD), right (RCA) and circumflex (LCX) coronary arteries. See Cerqueira et al., *Standardized Myocardial segmentation and nomenclature for tomographic imaging of the heart: A statement for healthcare professionals from the cardiac imaging committee of the council on clinical cardiology of the American Heart Association*, Circulation: 105: 539-542 (2002). The model can be displayed on the physician workstation (or electronically stored in memory at a suitable local or remote site) as a color-coded graphic display in any suitable format, such as, but not limited to, GIF, TIFF, JPEG or BMP. The model 500 can be configured to display adjacent one or more histograms of different slices of intensity data at a physician workstation. The 17 compartments can be those listed below.

1. basal anterior
2. basal anteroseptal
3. basal inferoseptal
4. basal inferior
5. basal inferolateral
6. basal anterolateral
7. mid anterior
8. mid anteroseptal
9. mid inferoseptal
10. mid inferior
11. mid inferolateral
12. mid anterolateral
13. apical anterior
14. apical septal
15. apical inferior 16. apical lateral
17. apex It is contemplated that employing the standardized model using CMR data alone or with data from other techniques can provide additional information in the process of myocellular injury in patients having or at potential of having (global) cardiac injury, for example, patients receiving chemotherapy. Further, a determination of the relationship between regional myocellular injury and global LVEF change may be established. For example, in ischemic cardiomyopathy, injury to the apical LV segments is associated with reduced exercise capacity and an increased incidence of future myocardial infarction or death when compared to injury in basal myocardial segments.

Figure 14:
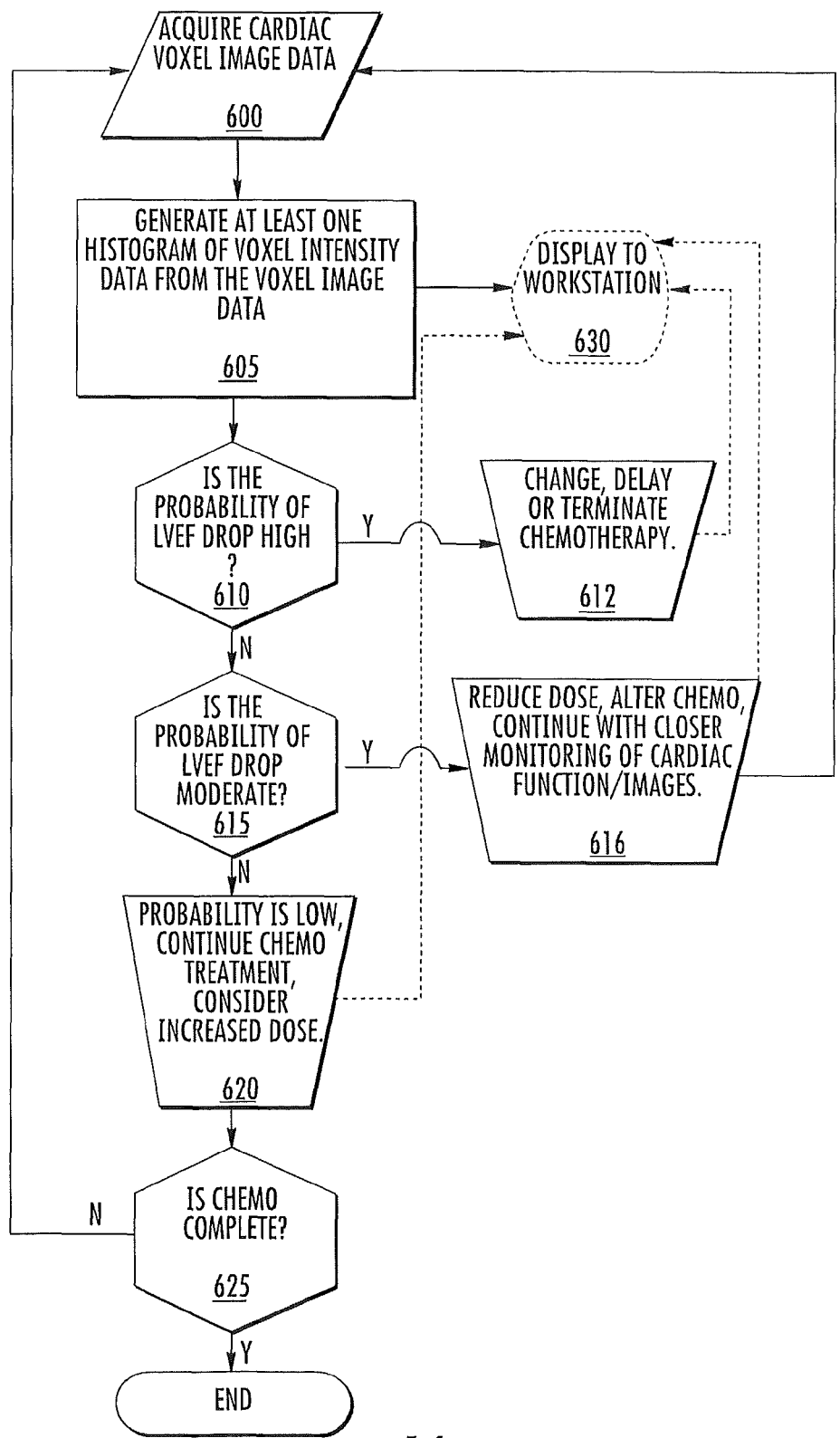
FIG. 14 is a flow chart of operations that can be carried out according to embodiments of the present invention.

FIG. 14 illustrates a non-invasive monitoring tool (which can be compared to a non-invasive biopsy) that can be used during a course of treatment of an oncology patient to monitor cardiotoxicity. As shown, cardiac image voxel data can be acquired (block 600). The image typically includes an image of at least the left ventricle myocardium. At least one histogram of the image data can be generated from the voxel image data (block 605). The histogram can be of intensity (average, mean or other measure of intensity) voxel distribution in regions of interest across the volume of the left ventricle myocardium including one or more of the apex, base or mid regions. In particular embodiments, a mean intensity histogram can be generated. An algorithm can electronically analyze the histogram data and determine if the probability of LVEF drop is high (block 610). In some embodiments, the algorithm can electronically evaluate a tail portion of the histogram to determine the probability of a future undesirable drop in LVEF, if chemotherapy is continued. The algorithm can include pattern recognition or electronic correlation analysis software that can analyze one or more of a line shape, distribution pattern, and/or histogram shape (particularly of the tail portion of the histogram). If the probability is high, then the clinician can be notified to determine if the chemotherapy should be changed (block 612). A clinician (such as an oncologist or other physician) may then decide how to proceed before the next planned active chemo delivery, such as, for example, decrease the dose, change the drug or drug combo, delay the next treatment, prescribe a medicament to help alleviate the condition, or terminate the chemo altogether (perhaps initiating an alternative treatment, such as a radiation treatment). If the probability is determined to be moderate (block 615), then a clinician can determine whether to decrease the dose, alter the chemotherapy regimen, change the chemotherapy drug(s), or increase the monitoring frequency (block 616). If the probability is considered low (block 620), the chemotherapy can continue as planned, and/or a physician may even increase the dose as needed. If the next round of chemotherapy is not the last, the sequence of operations described above can be repeated. The sequence of operations may be carried out at 1 month, 2 months and 4 months into chemotherapy and may include a baseline evaluation prior to initiation of chemotherapy.

As shown, optionally, the histogram results can be provided to a display associated with a clinician's workstation and/or each of the probability calculations and/or results can be provided to the display as well (block 630). The relative or absolute "high", "moderate" and "low" probabilities can be defined in any appropriate absolute or relative manner. However, "high" probability typically means that the likelihood that an undesired drop in LVEF (it is contemplated that the undesired drop may correlate to at least about a 5% LVEF drop, and typically (clinically) about 10% or more) will occur if the planned chemotherapy continues is about 75% or greater. The term "moderate" means between about 25%-74% probability that the LVEF drop will occur, and the term "low" means that there is less than about a 25% chance that the LVEF drop will occur.

The chemotherapy monitoring tool can be configured to consider factors other than the histogram to determine risk: for example, the type of chemotherapy regime, the number of doses received at the time of the reading, previous cardiac history, and the like. For example, about 85% of patients experiencing toxicity will do so after receipt of approximately 100 mg/m$^2$ of doxorubicin (usually at T=1 month). Thus an evaluation before that time that indicates a moderate risk may be elevated to a probable risk for future events. That is, if a patient presents with a "moderate" probability risk at baseline, after a first dose, and/or when associated with a drug or drug combination known to induce more severe cardiotoxicity reaction, then this data may be considered to make the patient at high risk for the planned chemotherapy treatment.

Because the monitoring is non-invasive, a clinician can request daily, weekly, monthly, or at other desired schedules of review and may even use the monitoring data to help time the spacing and/or date of the chemotherapy delivery itself and/or to titrate a dose for that patient.

The operations can be carried out to generate a report of probabilities of cardiotoxicity response. The report can be an electronic and/or paper report, and may be generated in substantially real-time or shortly after acquisition of the image data. A first baseline image can be obtained prior to initiation of a chemotherapy regime. Alternatively, one or more monitoring images can be obtained at various times during the course of chemotherapy. In some embodiments, a respective image can be obtained and the LVEF drop predictive analysis performed before each round of chemotherapy, particularly each later round of chemotherapy. Alternatively, the analysis can be carried out after (or even during) a chemotherapy administration. The monitoring process can generate an alert to notify a physician if a probability is high or moderate, before irreversible injury associated with an undesired drop in LVEF actually occurs. This alert of probabilities of an undesirable response can allow a clinician to alter the planned therapy before actual irreversible LVEF injury occurs.

While embodiments of the present invention have been described above with respect to particular views, regions, areas and/or slices of the heart, other views, regions, areas and/or slices of the heart may also be utilized. Furthermore, fewer or greater than three slices may be utilized. Different numbers of slices may be used for different patients. For example, three slices may be appropriate to sufficiently evaluate a heart of a young child, while about 20 may be required for a heart of a large person, with an average number of slices being about 10.

Additionally, the images may be taken along the long or short axis of the heart. Accordingly, certain embodiments of the present invention should not be construed as limited to the particular views of the heart but may include any view and/or number of views of the heart that allow for intensity analysis to detect global cardiac injury.

Typically, a first baseline image will be obtained prior to or early in treatment or as an initial reference point in diagnosis of change in cardiac condition. Subsequent images for comparison may be taken daily, weekly or at other fixed or variable interval(s) or prior to or after a planned treatment, such as a cytotoxic treatment.

It is noted that although for some embodiments including voxel data from the left ventricle of particular interest in assessing cardiac injury and/or cardiotoxicity has been described above, voxel data from other regions of the heart, including for example, the right ventricle and/or the base or tip may be employed. Combinations of two or more spaced apart regions of interest in different heart locations may also be used to evaluate cardiac injury and/or risk of injury. The region(s) so selected, when having impaired or dead cells identified by image voxel data, can be associated with reduced cardiac function and/or a present or future increased risk of cardiac dysfunction or even cardiac-induced morbidity.

It is contemplated that voxel data can help identify impaired cells as well as necrotic tissue. That is, in some embodiments, voxel data can be used to visualize or detect cell injury, such as that associated with inflammation or accumulation of water around cells in the heart, which can inhibit contractility and impair cardiac function. The impaired cell data can also be used to predict future irreversible cardiac injury or a more severe drop in function or contractility, oxygenation, valve function and the like.

In some embodiments, a clustering of impaired or dead cells in one or more volumetric regions of interest can be used to indicate present cardiac injury and/or predict future cardiac injury associated with undesirable cardiac dysfunction. The clustering-effect may have more relevance for less voxels having less intensity than "super hot" voxels (super-hot refers to the highest intensity voxels), such as, for example, where clusters of relatively mid-intensity voxels or mid-high intensity voxels appear in certain compartments of the heart. See, e.g., the arrows that point to exemplary range voxels in FIG. 16.

It will be appreciated that although described above primarily with respect to cardiotoxicity induced by chemotherapy, the evaluation techniques described herein can be used for other medical evaluations of cardiac injury and/or cardiotoxicity due to other conditions, injuries or other toxic exposures. For example, embodiments of the present invention can evaluate cardiotoxicity associated with one or more of environmental toxin exposure (airborne, water, waste, and the like), poison (including insect, snake or other venoms), prescription or non-prescription drugs, and the like.

Some embodiments of the invention may be used to evaluate how drugs affect cardiac tissue for pharmacological studies, such as, for example, clinical trials and/or drug discovery.

Figure 20:
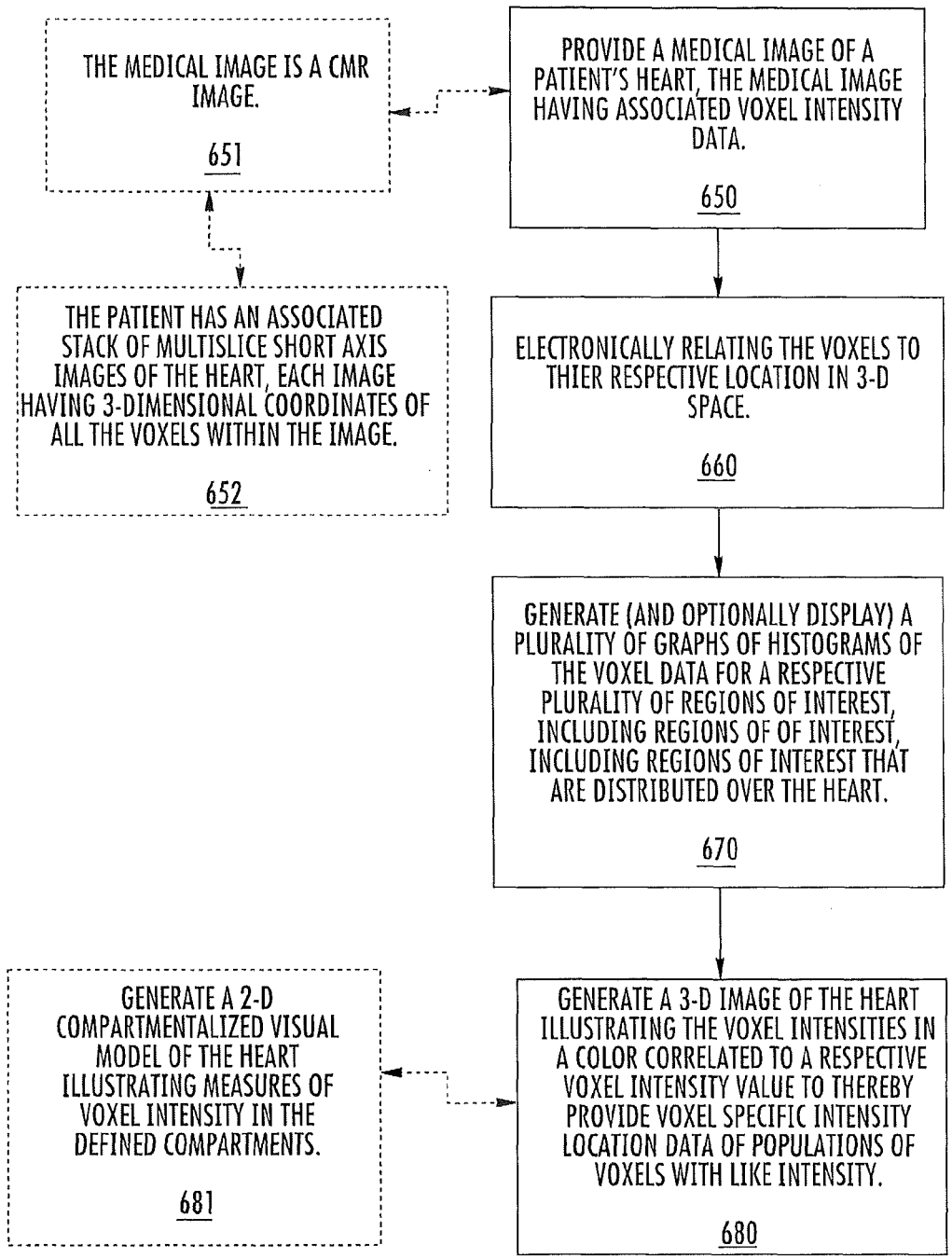
FIG. 20 is a flow chart of operations according to certain embodiments of the present invention.

Turning now to FIG. 20, embodiments of the present invention provide a visual tool of diagnostic data of a 3-D volume of the heart to allow a physician interface for ease of viewing cardiac injury, such as global injury that can occur with cardiotoxicity. The 3-D image can visually illustrate (typically in color) populations of similar intensity voxels (voxel intensity distribution) in the heart. As shown in FIG. 20, a medical image of a patient's heart is provided, the image having associated voxel intensity data (block 650). The medical image may optionally be a CMR image (block 651) and may have a stack of multi-slice short axis images, each image having 3-D coordinates of all the voxels within the image (block 652). The voxels can be electronically related to a respective location (in the heart) in 3-D space (block 660). A plurality of histograms of the voxel data for a plurality of regions of interest, including regions that are distributed over the heart, can be generated (and optionally displayed) (block 670). A 3-D image of the heart can be generated (and displayed) illustrating the voxel intensities in a color correlated to a respective intensity value to thereby provide voxel-specific intensity and location data of locations of populations (of similar intensity) of voxels over the heart (block 680). In this manner numbers and relative spatial location of similar intensity voxels can be relatively easily determined, allowing a clinician to view where and how much of the heart is affected by cell injury and/or death.

Diagnostic data that can be provided by the 3-D voxel evaluation that may be of clinical interest include location and numbers of voxels having intensity measures indicative of injury or cell death. This is because even small numbers of voxels of undesirable intensity may be associated with a decrease in function (such as pumping) if located in a susceptible area/region of the heart. On the other hand, even if not located in a relatively susceptible region of the heart, a relatively large number of voxels of undesirable intensity (even if not tightly or even loosely clustered) may also be problematic or predictive of a cardiac state. The voxel distribution may reveal a small number of high intensity voxels (which may be particularly relevant if located within a critical region associated with heart malfunction), a large number of clustered voxels of undesired intensity (representing cellular injury or death) in one or more locations, a lower number of clustered voxels when disposed in a critical zone or region, a sprinkling of voxels, or a sprinkling of clusters of voxels, if the voxels or clusters are relatively closely spaced in a tissue region. If one or more of the above is present, cardiac injury, impairment or cardiac dysfunction may be indicated.

If displayed, the histograms can be visually presented in color in a format that allows a clinician to relatively quickly scroll through a series of the histograms for a visual review of the distribution of intensity in the heart. The histograms can be configured to show graphs of regions of interest as a percentage of the entire 3-D volume.

In some embodiments, a 2-D compartmentalized visual model of the heart illustrating measures of intensity in the defined compartments can be displayed (block 681) and may be stored electronically and/or printed in paper for a patient's file. In some embodiments, an evaluation or prediction of an outcome or condition of interest (LVEF, indicator variables or parameters for LVEF drop or other serum markers of heart injury) can be carried out using intensity measures in one or more of the compartments. Positive match of an undesired voxel intensity distribution extending in multiple segments or compartments may be predictive of cell injury, cell death and/or cardiac injury.

Figure 21:
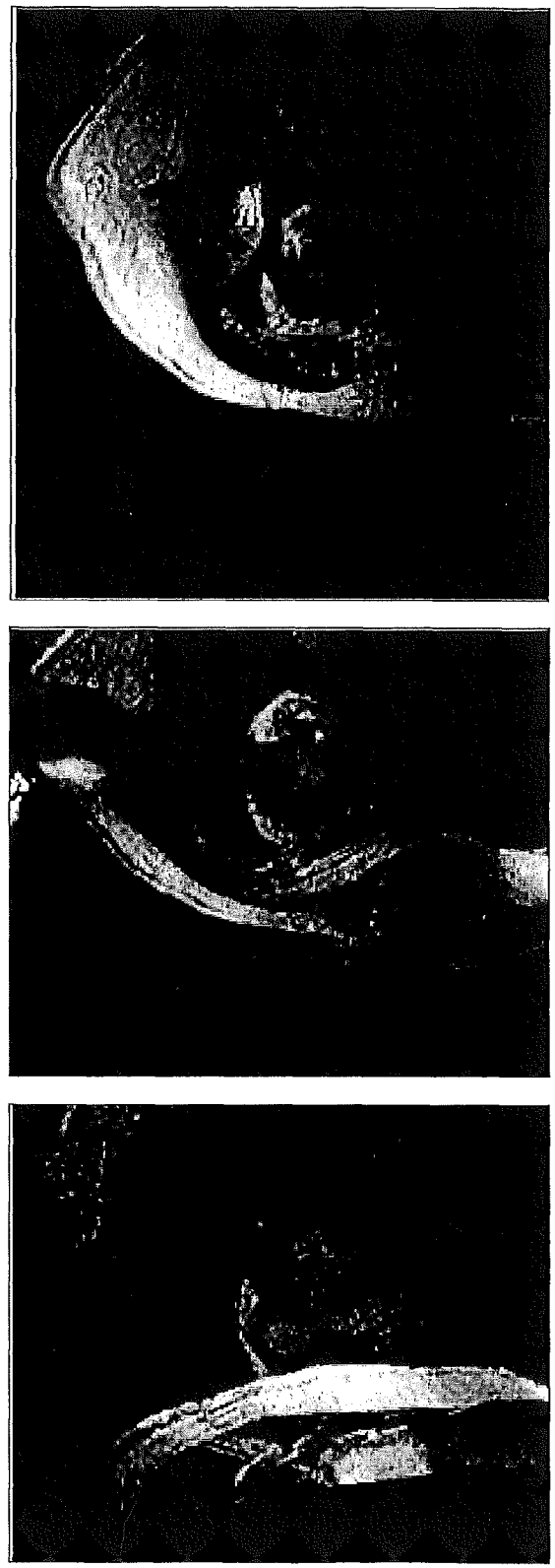
FIG. 21 is an exemplary screen shot of 3-D images of the heart with populations of voxel intensities shown according to embodiments of the present invention.
Figure 22:
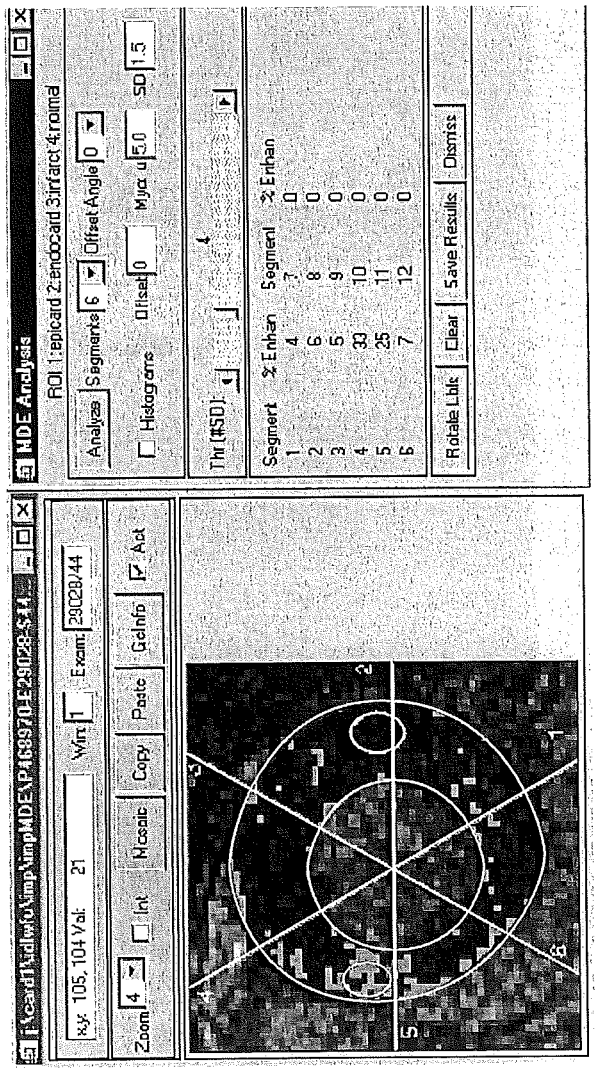
FIG. 22 is an exemplary screen shot of a 2-D compartmentalized model of the heart with intensity data provided based on records providing 3-D voxel data according to embodiments of the present invention.
Figure 23:
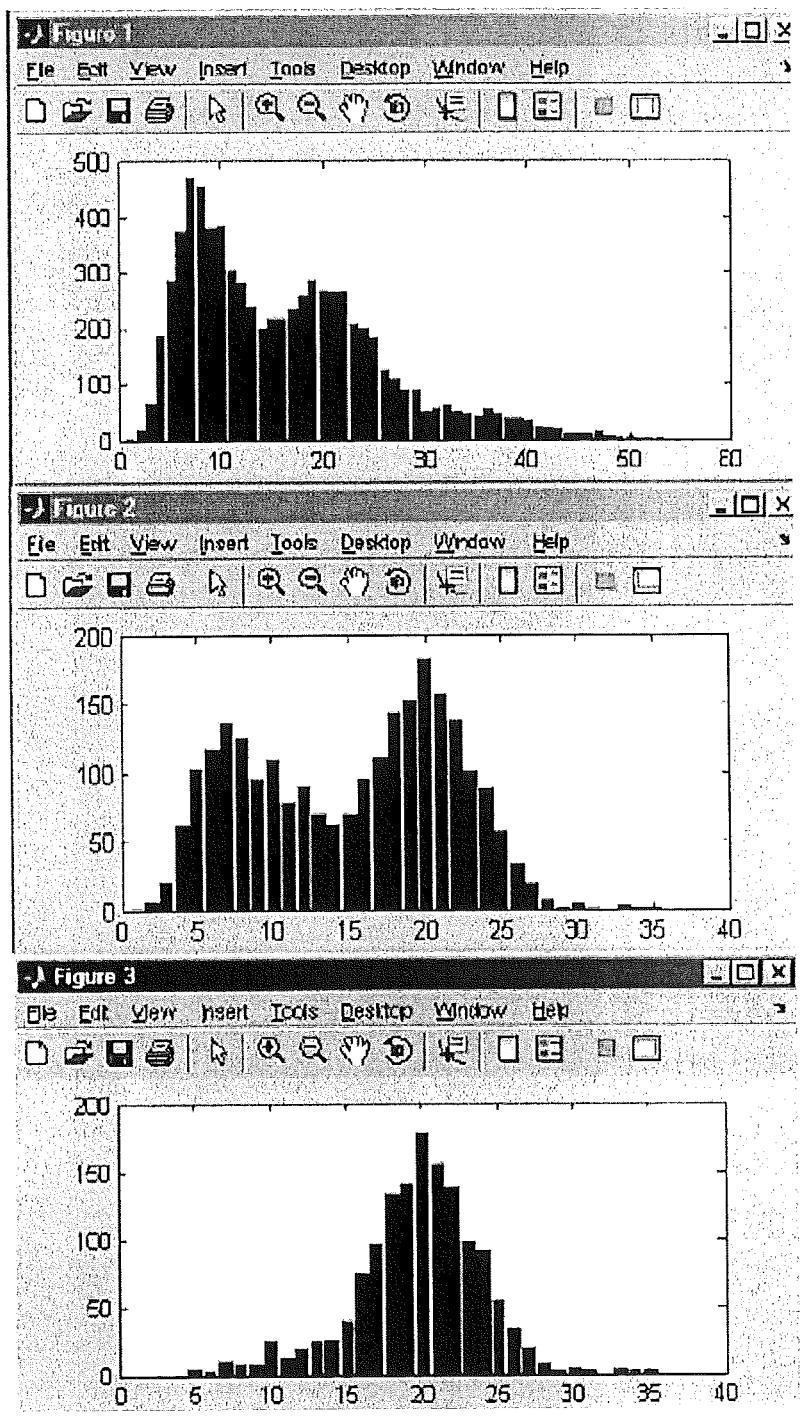
FIG. 23 is an exemplary screen shot of a set of histograms shown on a display of a workstation providing a clinician reference tool corresponding to data from the images shown in FIG. 21, according to embodiments of the present invention.

FIG. 21 is an exemplary screen shot of 3-D images of the heart with populations of voxel intensities shown according to embodiments of the present invention. FIG. 21 includes three screen shots of a short axis view of the left ventricle where white/lighter regions in the screen shot of the images indicate high intensity voxels. The middle slice reveals an area of infarction. FIG. 22 is an exemplary screen shot of a 2-D compartmentalized model of the heart with intensity data provided based on records providing 3-D voxel data according to embodiments of the present invention. The image can be in color to visually emphasize the locations of high intensity pixels in the image. For example, "normal" pixel intensities can be represented in gray scale while high intensity pixels may be shown in green or some other visually enhanced color for ease of visualization. FIG. 23 is an exemplary screen shot of a set of histograms shown on a display of a workstation providing a clinician reference tool, according to embodiments of the present invention. The histograms shown in FIG. 23 correspond to the voxel intensity in ROIs in the images shown FIG. 21.

Figure 24:
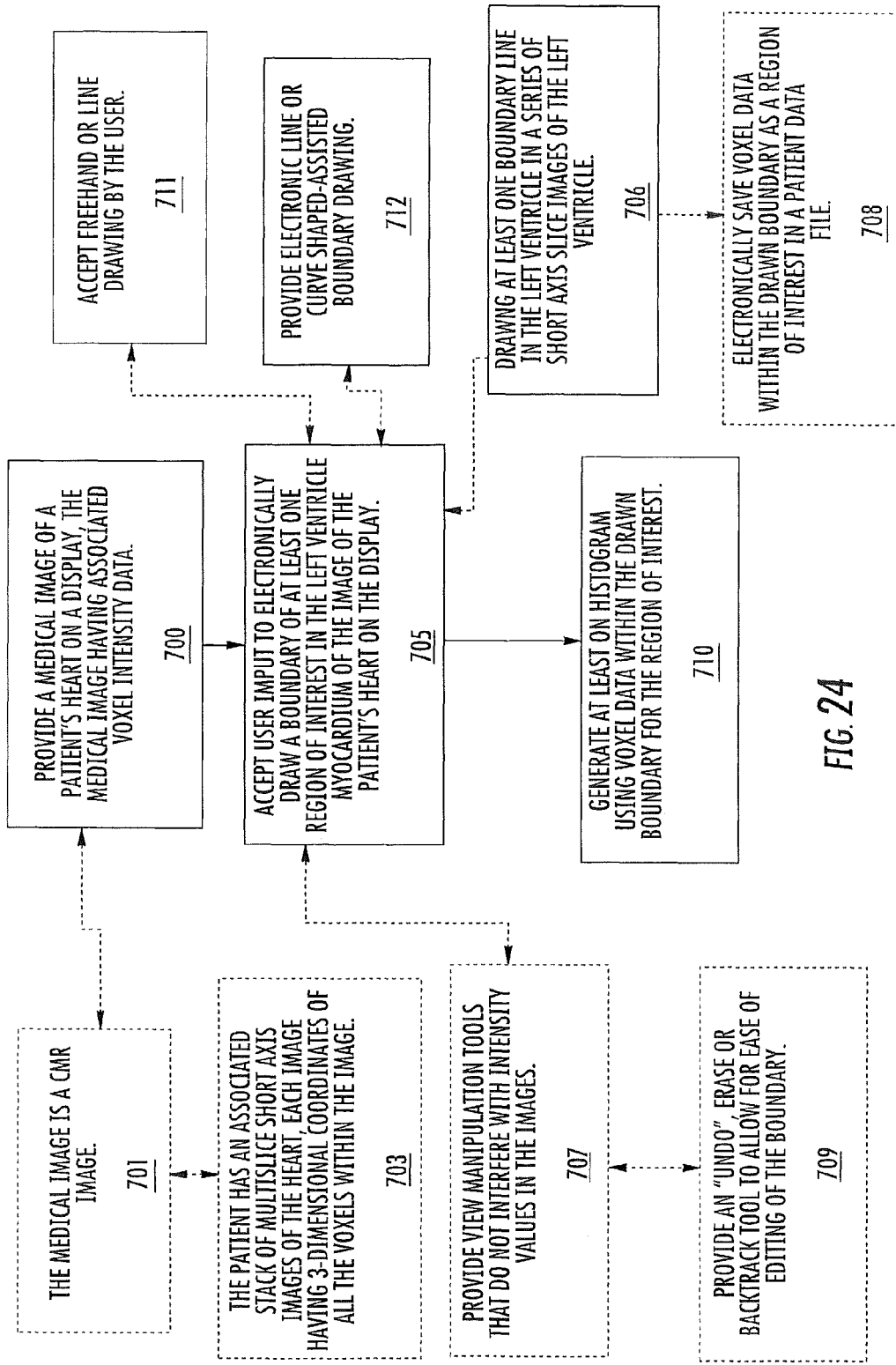
FIG. 24 is a flow chart of operations according to certain embodiments of the present invention.

FIG. 24 is a flow chart illustrating yet other embodiments of the present invention. In this embodiment, a medical image of the heart can be provided to a display (the image having associated voxel intensity data) (block 700). User input is accepted to electronically draw, using the display, a boundary of at least one region of interest in the heart (block 705). The region of interest can be a three-dimensional region having an associated thickness. The at least one region of interest can be the left ventricle myocardium and the user can draw the line as a series of short axis images of the heart (as the region has an associated thickness) (block 706). At least one histogram of voxel intensity data can be generated using voxel data within the drawn boundary for the region of interest (block 710).

The image can be a CMR image (block 701) that can include a stack of short axis image views of the heart; each image can have 3-D dimensional coordinates of all the voxels within its image (block 703).

The user input can be by freehand (manual) drawing (block 711) using a finger contact on the screen, a stencil, light beam, or other input tool. Alternatively, or additionally, the user input can include selectable tools, such as electronically assisted line or curve shape-assisted boundary drawing features, including, for example, spline format tools (block 712). Manipulation tools that allow the user to move a drawn line or inserted point, adjust the shape or size, zoom, rotate or otherwise manipulate the image and/or the drawn boundary line can be provided in a manner that does not interfere with intensity values in the images (block 707). An "undo", erase or backtrack tool can be provided to allow ease of editing the drawn boundary (block 709).

In some embodiments, voxel data can be related to the region of interest within the drawn boundary and electronically saved to a patent data file (such as on a patient database record server) (block 708).

Figure 25:
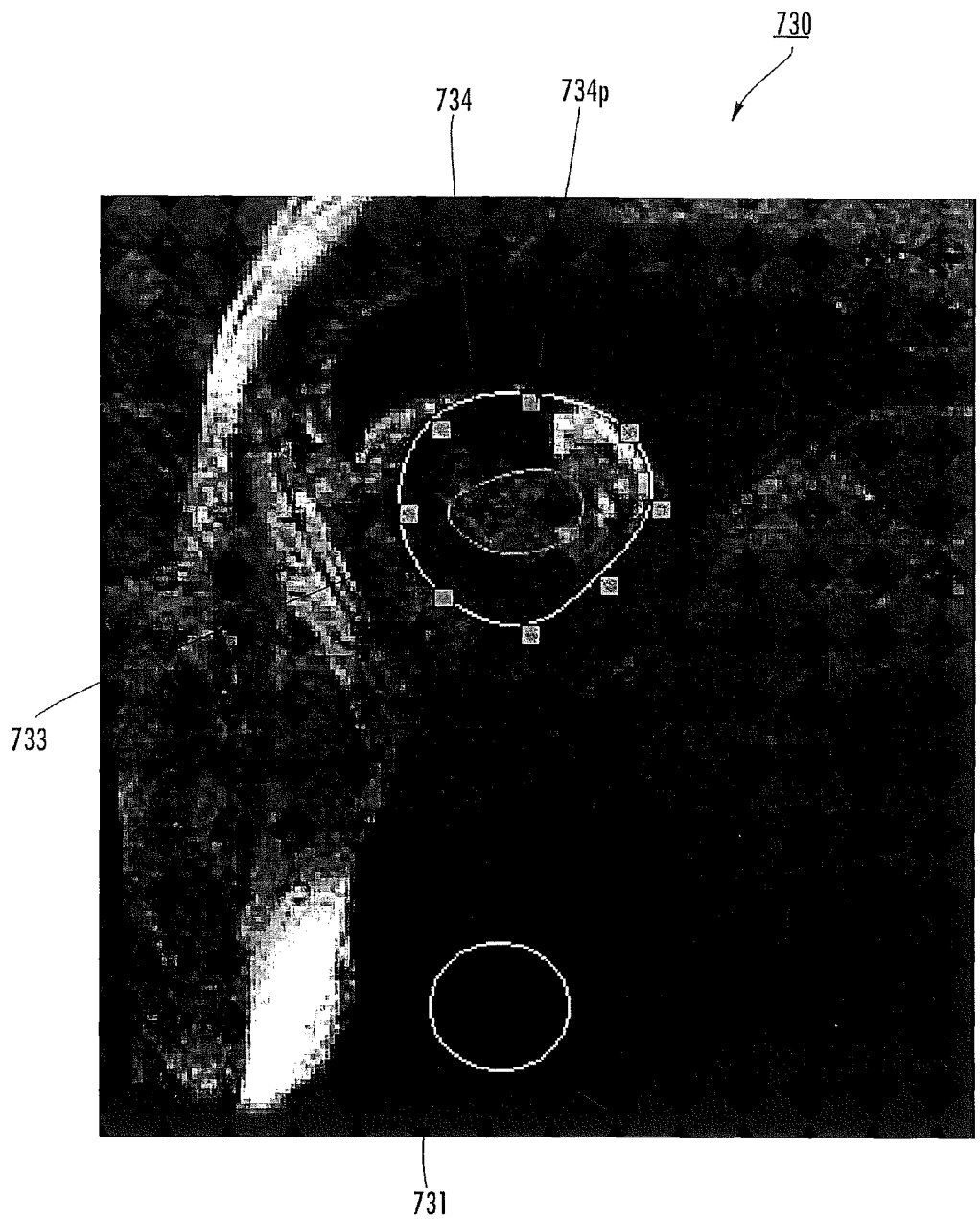
FIG. 25 is a screen capture of a boundary drawn on a medical image on a display using a GUI boundary-drawing tool according to embodiments of the present invention.

FIG. 25 illustrates a display 730 with an image of the heart and a defined region of background noise in the air 731 with a user drawn inner boundary 733 and user positioned points 734*p* spaced apart about an outer boundary 734 of a left ventricle annular space. Thus, the cardiac evaluation systems can be configured to allow a user to trace or draw an annulus encompassing the left ventricle myocardium as two separate closed curves. The inner boundary line 733 is drawn about the endocardial surface and the outer boundary line 734 is drawn about the epicardial surface. In this image, the left ventricle is of particular interest but other regions may be of interest and a user/operating drawing of boundaries may also be used in other regions of interest.

The epi- and endocardial border (or other feature) of each slice from a multi-slice short axis acquisition can be identified using a contour following, gradient based semi-automated drawing program according to generally known digital image processing techniques. See, e.g., Pratt W. K., *Digital Image Processing*, NY, N.Y. (2d ed.), John Wiley and Sons; 1991; 610-22. Basal slices can be reviewed in cine format to resolve structures for inclusion (aortic outflow tract) or exclusion (left atrium and mitral leaflets).

The user drawn or defined curves can be drawn using closed splines or freehand. Re-size handles (shown as the squares) enclosing points 734 can be used on a selected curve to provide ease of adjustment of size and/or shape. The proposed boundary drawing techniques can help to avoid partial volume effects associated with high signal intensities found within the blood pool of the LF cavity or in pericardial fluid external to the myocardium. Thus, a semi-automated method as described can allow a user/operator to delineate the boundaries of anatomical structures in the heart, such as to delineate the endocardial epicedial surfaces in a time efficient manner.

In some embodiments, software or algorithms can be used to perform a region-growing operation to identify the voxels contained within the indicated boundaries. The voxel intensities and respective (x, y, and z) coordinates can be electronically saved to a patient file, such as a local or remote server and/or disk file, and may be held in the same folder as the image data or just correlated using an assigned digital address or other suitable correlating technique. The data can be written in text, EXCEL or other suitable formats.

It will be appreciated that each LV short axis slice can include between about 2,000-20,000 voxels (typically depending on slice location), defining the location and correlation of the location to the voxel intensity data can help assess a change in signal intensity in voxels in regions of interest, as the change can be predictive of a cardiac injury. Identification of the voxels within the LV myocardium versus voxels physically located in other structures (valves), or cavities (LV chamber) and/or blood pools, can provide increased reliability in the analysis model. Similarly, characterizing background noise may be useful, as the noise typically exists within the image; characterizing the background noise and adjusting for it as appropriate may facilitate the voxel intensity analysis.

In some embodiments, noise removal can be carried out by subtracting the histogram of the air ROI, shown for example as feature 731 in FIG. 25). The ROI for the air region 731 can be automatically electronically sized so that it has the same area (and hence the same number of voxels) as the annular LV ROI. The scaling can facilitate proper subtraction of the air histogram from the LV ROI histogram in a noise removal process. Histograms of voxel intensities in the LV or air regions, as well as a difference histogram, can be graphed using flexible plot features, such as customized plotting features provided by MATLAB. The plots or graphs can be electronically stored in the patient files.

Figure 26A:
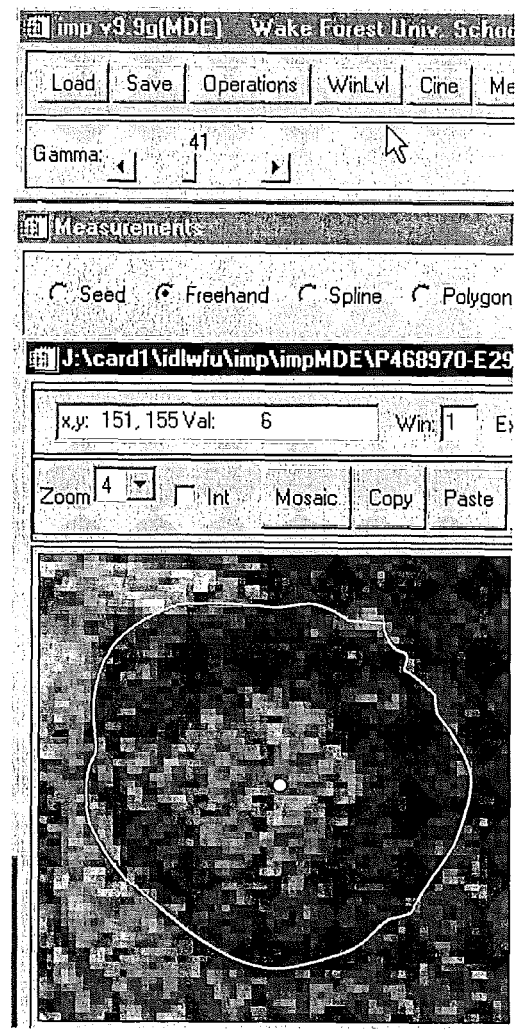
FIGS. 26A, 27A, and 28A illustrate screen captures with boundary lines and/or drawing tool "dots" electronically enhanced using Microsoft® Paint for visibility.
Figure 26B:
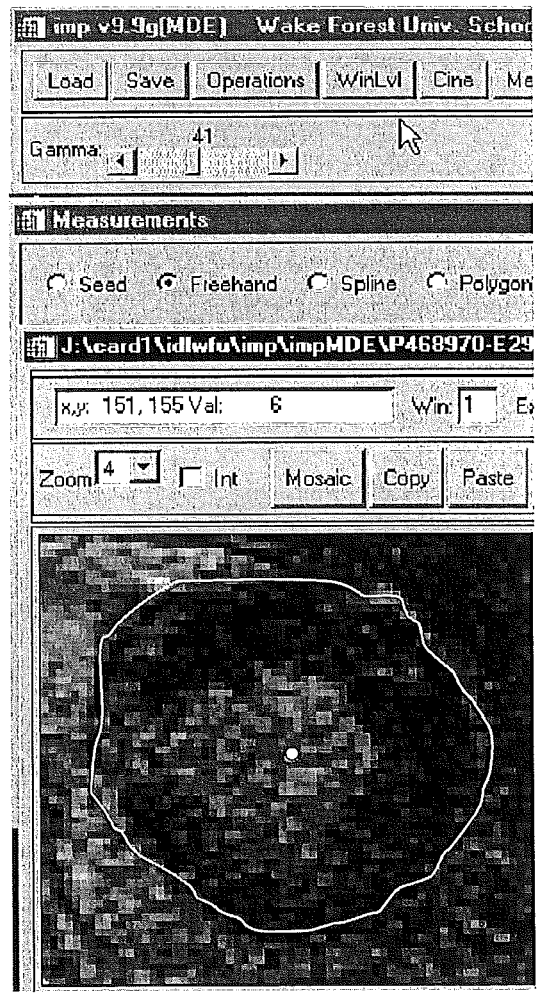
FIGS. 26B, 27B, and 28B are screen captures with exemplary interactive border/line drawing tools capable of generating color lines on a display according to embodiments of the present invention.
Figure 27A:
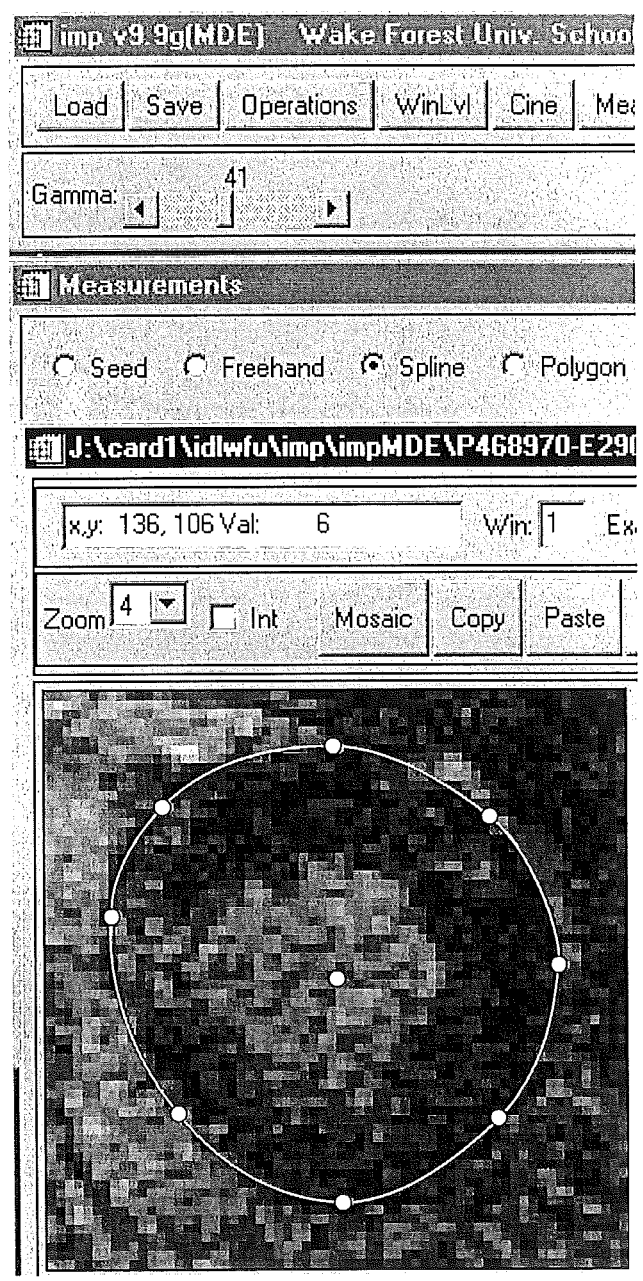
Figure 27B:
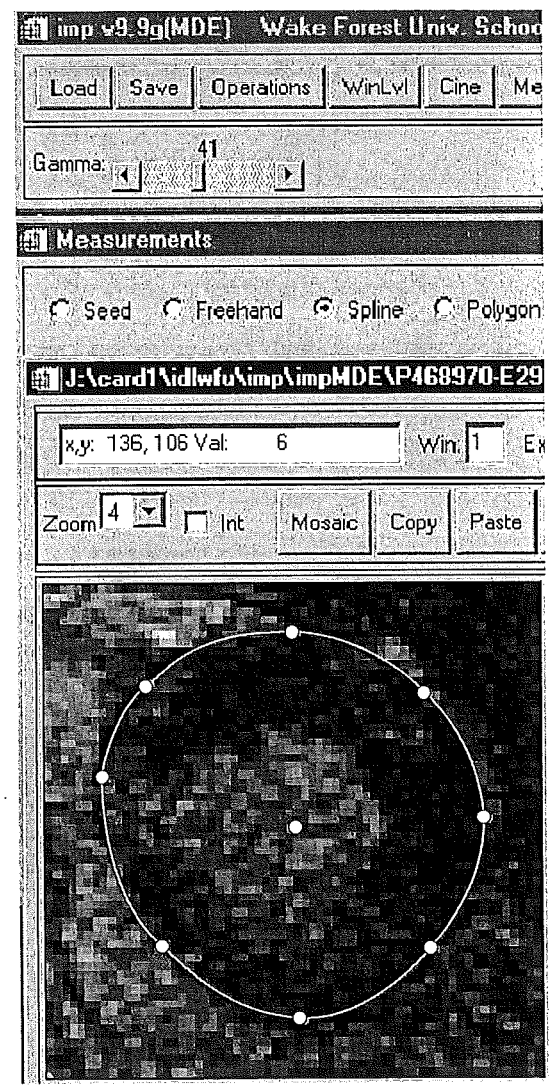
Figure 28A:
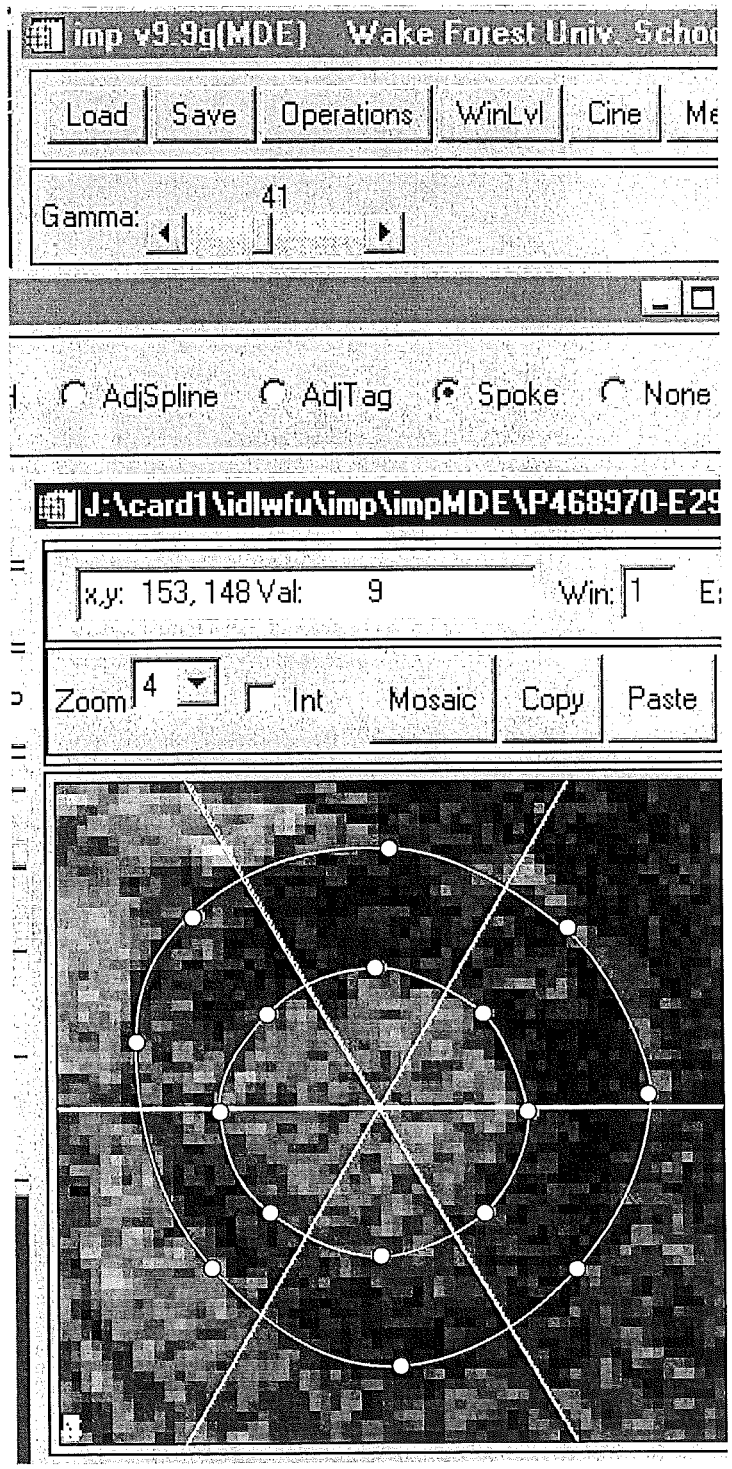
Figure 28B:
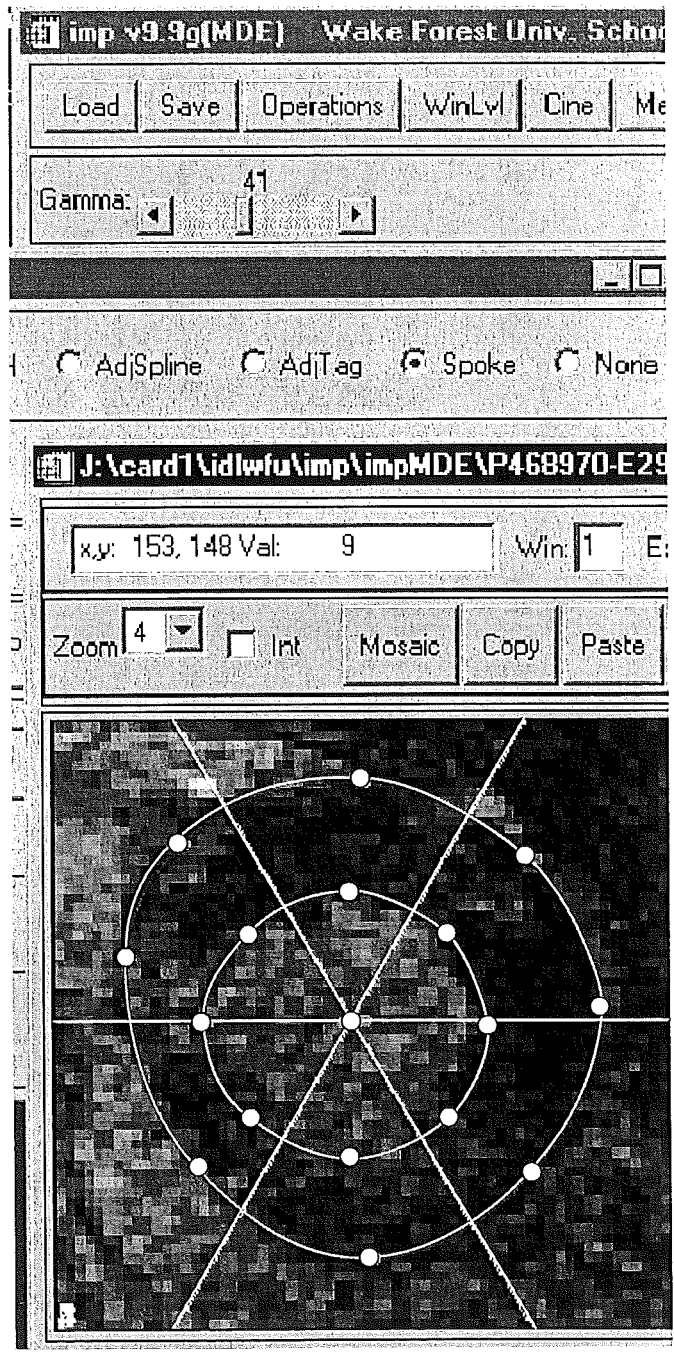

FIGS. 26B, 27B, and 28B are screen captures of exemplary interactive border/line drawing tools (with the thin (drawn) boundary(ies) in red) according to embodiments of the present invention. FIGS. 26A, 27A and 28A show the respective screen captures in black and white with the line thickness increased and intensity of dots enhanced using Microsoft® Paint for ease of viewing/reproduction. FIGS. 26-28 are mid short-axis views with intensity variations in the left ventricle. FIGS. 26A, 26B illustrates a screen shot with a "freehand" drawing tool selected and used to draw a boundary line in a region of interest. FIGS. 27A, 27B illustrates a "spline" tool selected with the dots on the boundary representing the adjustable spline drawing tool, FIG. 28A, 28B illustrate a "spoke" tool selected and two boundary lines drawn in the image (an inner perimeter and outer perimeter boundary line). The image can be segmented in a number of ways, shown as segmented into 6 compartments (drawn by the lighter or white line (FIG. 28A) or yellow line (FIG. 28B) dividing the region of interest shown). The number of compartments can be adjusted to include greater or lesser compartments (i.e., 4-12 or less or even more) or set to a standard model such as that shown in FIG. 13 (i.e, an apical view can include 4 segments). The compartments can be drawn to be equally divide the region of interest or to include unequal divisions of a region of interest.

FIGS. 29A-29C are schematic illustrations of exemplary different GUI input formats that can be used to draw or trace boundaries in a medical image according to embodiments of the present invention. FIG. 29A illustrates a display 730' with a user input with a pull down trace menu of shapes 731 that can be selected then electronically placed about features in a region of interest. The shape can be resized and shaped using different editing tools. FIG. 29B illustrates a display 730' with a menu 731 for freehand or manual drawing of a boundary or line. Editing tools for draw/retrace, back (typically incrementally back), redo/erase can also be provided as shown. FIG. 29C illustrates a display 730' with a menu 731 of tools including points that can be positioned about the target region, including a draw button that can be used to connect the points to define the border, and the like. Draw, redraw and "point" anchor inputs may be provided as well. The editing tools can be via menu, or toolbars, or manual tracing and may also employ mouse or keyboard input.

Figure 30:
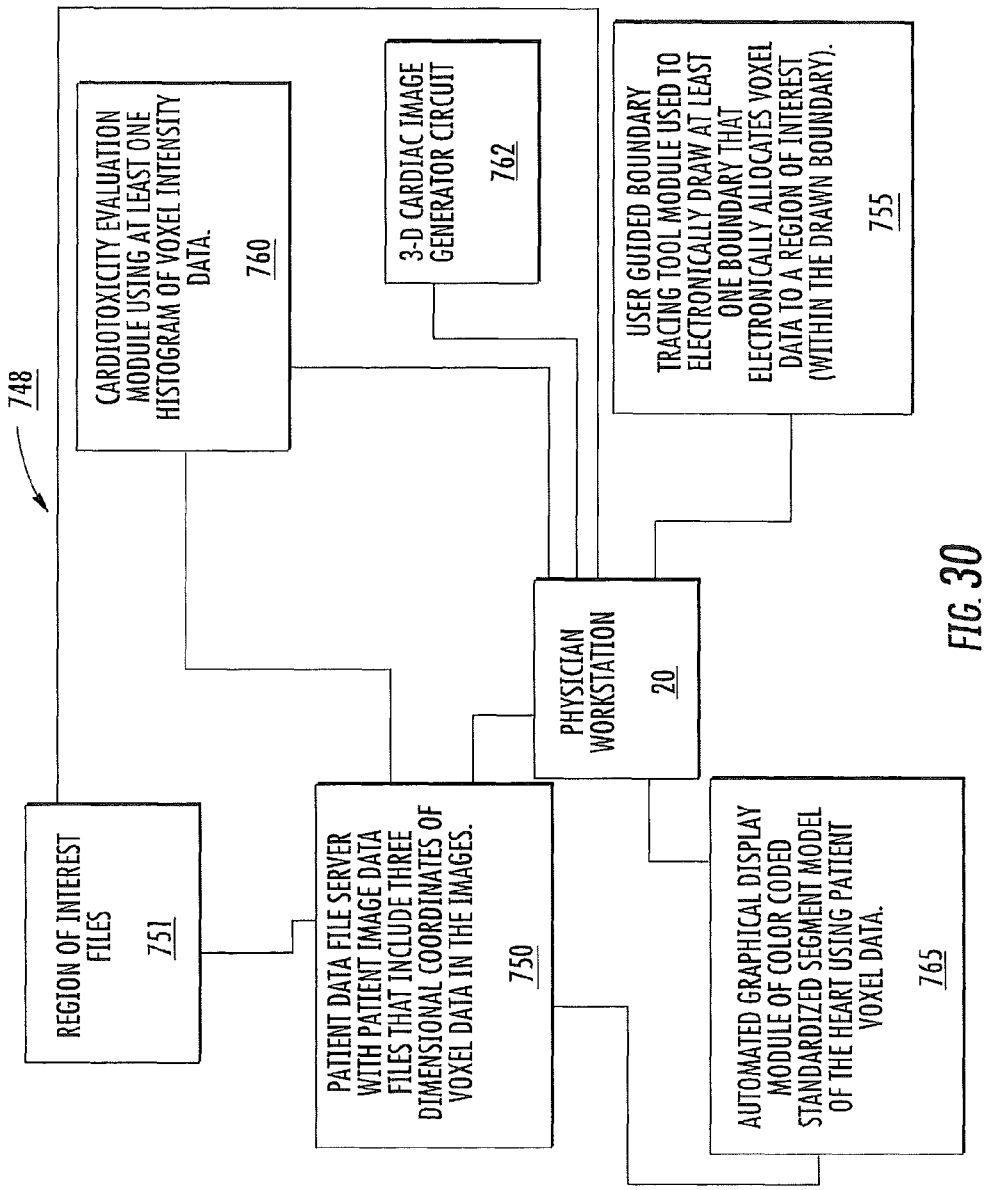
FIG. 30 is a schematic illustration of a cardiotoxicity evaluation system according to embodiments of the present invention.

FIG. 30 is a schematic illustration of a cardiotoxicity evaluation system 748 according to embodiments of the present invention. As shown, the system 748 is in communication with a workstation 20. The system 748 includes a patient data file server 750 that has patient image data files that include three-dimensional coordinates of voxel data in regions of interest in the image. The region of interest files 751 may be held or stored as a subset of separate electronic files or folders 751 or may be integrated into the master image voxel files of the patients. The patient files may be on one or more servers. The system 748 also includes an automated graphical display module 765 that can generate a color-coded standardized segment model of the heart using patient voxel data. The system 748 may also include a cardiotoxicity evaluation module 760 that can employ data from at least one histogram of voxel intensity data. The system 748 can also include a user-guided boundary tracing tool module 755 that can accept user input to electronically draw at least one boundary that electronically associates voxel data to a region of interest within the drawn boundary.

Figure 31:
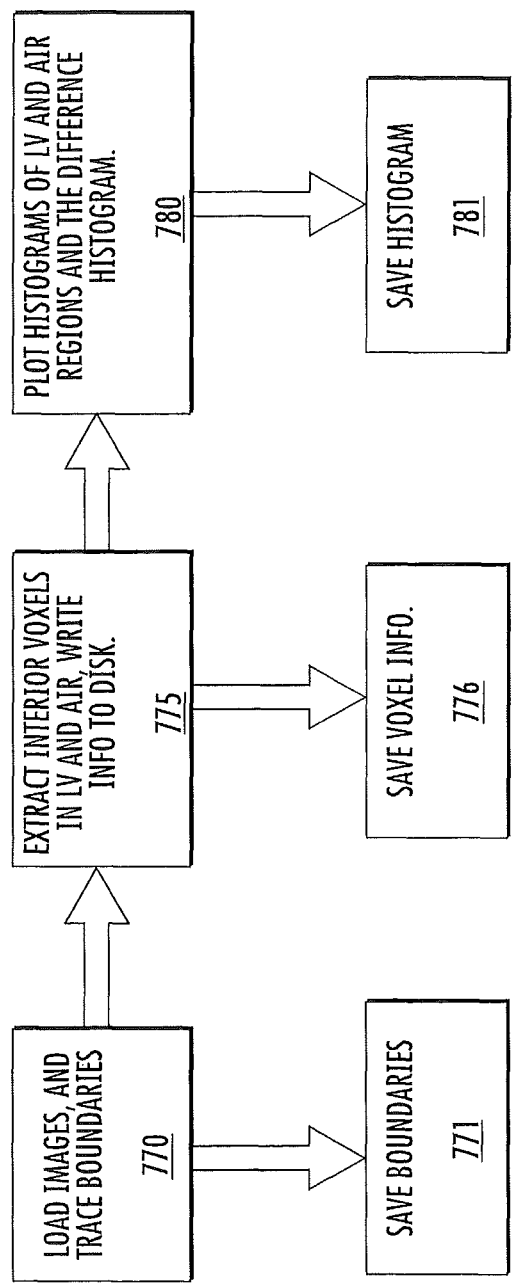
FIG. 31 is a flow chart of a process that can be used to extract left ventricle voxel data according to embodiments of the present invention.

FIG. 31 is a flow chart of a process that can be used to extract left ventricle voxel data according to some particular embodiments of the present invention. Images associated with a patient can be selected and loaded onto a workstation (for display at the workstation) (block 770). The defined boundaries in the images can be electronically saved (block 771) such as to a server, disk or other suitable device or medium. The interior voxels in the LV can be extracted as well as the voxels in air (for the noise calculation/adjustment) (block 775). The extracted voxel data can be electronically saved as noted for the boundaries (block 776). Histograms of LV and air regions can be plotted as well as a difference histogram (block 780). The histograms can be electronically stored as noted above (block 781).

The invention will now be described in more detail in the following non-limiting examples.

EXAMPLES

As briefly mentioned above, conventionally, identification of myocellular necrosis in patients with an ischemic cardiomyopathy has been performed by locating the voxels with a signal intensity >2 standard deviations above the background intensity within non-enhanced LV myocardium. The amount of necrosis is quantified by determining the transmural extent of hyperenhancement expressed as a ratio of the number of high intensity pixels extending linearly from the endocardial to the epicardial surface relative to the total distance from the endocardium to epicardium. Since myocardial necrosis proceeds in a wavefront from the endocardial to epicardial surface in the setting of reduced coronary arterial blood flow, this method is useful for assessing the amount of necrosis after myocardial infarction.

Figure 6:
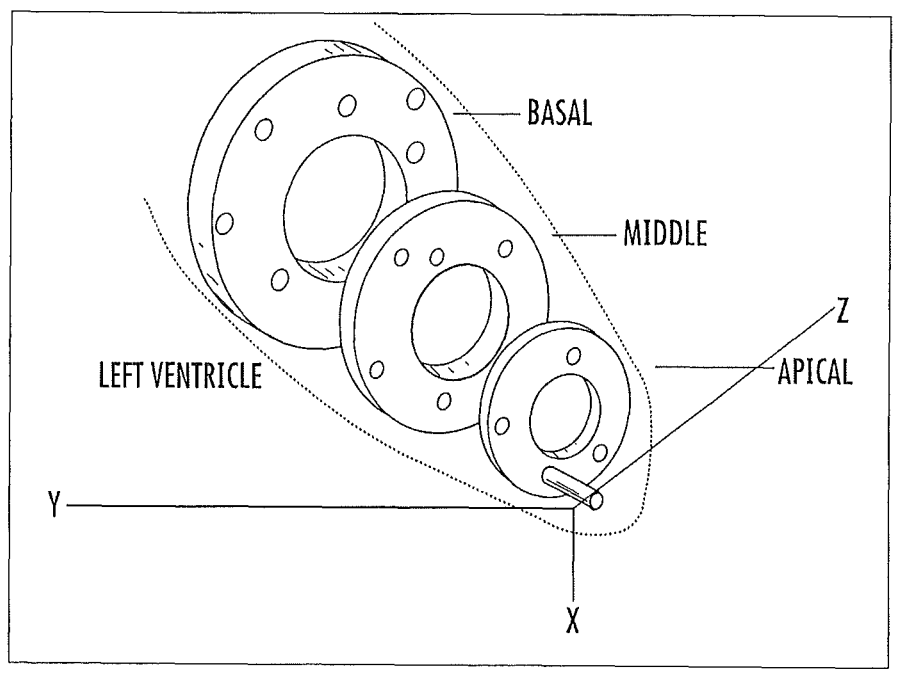
FIG. 6 is a three-dimensional depiction of three short axis planes of a left ventricle.

However, this method may not be as well suited for a process that causes necrosis to susceptible tissue throughout the LV myocardium in a randomly distributed pattern (e.g. a global injury). To overcome this limitation, voxels, and in some embodiments all the voxels, within three short axis slice positions (apex, middle, and base) within the LV may be sampled and the intensity and x, y, and z coordinates of each voxel identified in 3-dimensional space (FIG. 6). FIG. 6 is a 3-Dimensional depiction of 3 short axis (basal, middle, and apical) planes of the left ventricle. In each plane, the grid of small boxes on the face of each slice demarcate the voxels. During analysis, the image intensity of each voxel and the x, y, and z coordinates are recorded. In this way, high intensity pixels identified with the delayed enhancement technique associated with a randomly distributed process causing myocellular necrosis (white splotches on images) can be characterized.

Correction for variations in the intensity of voxels in the images may also be identified by determining the intensity of voxels within a target region, typically, a 1 cm diameter circular ROI placed outside the heart. For each apical, middle, and basal slice, the number of pixels at a given intensity may be determined and the intensity from the ROI external to the heart subtracted from the pixels. In certain embodiments, for each slice, the mean intensity of all voxels and the peak voxel intensity in the highest 40% of the distribution may be determined (FIG. 6). In this way, regions of high intensity pixels may be identified relative to their location within the left ventricle.

Figure 7:
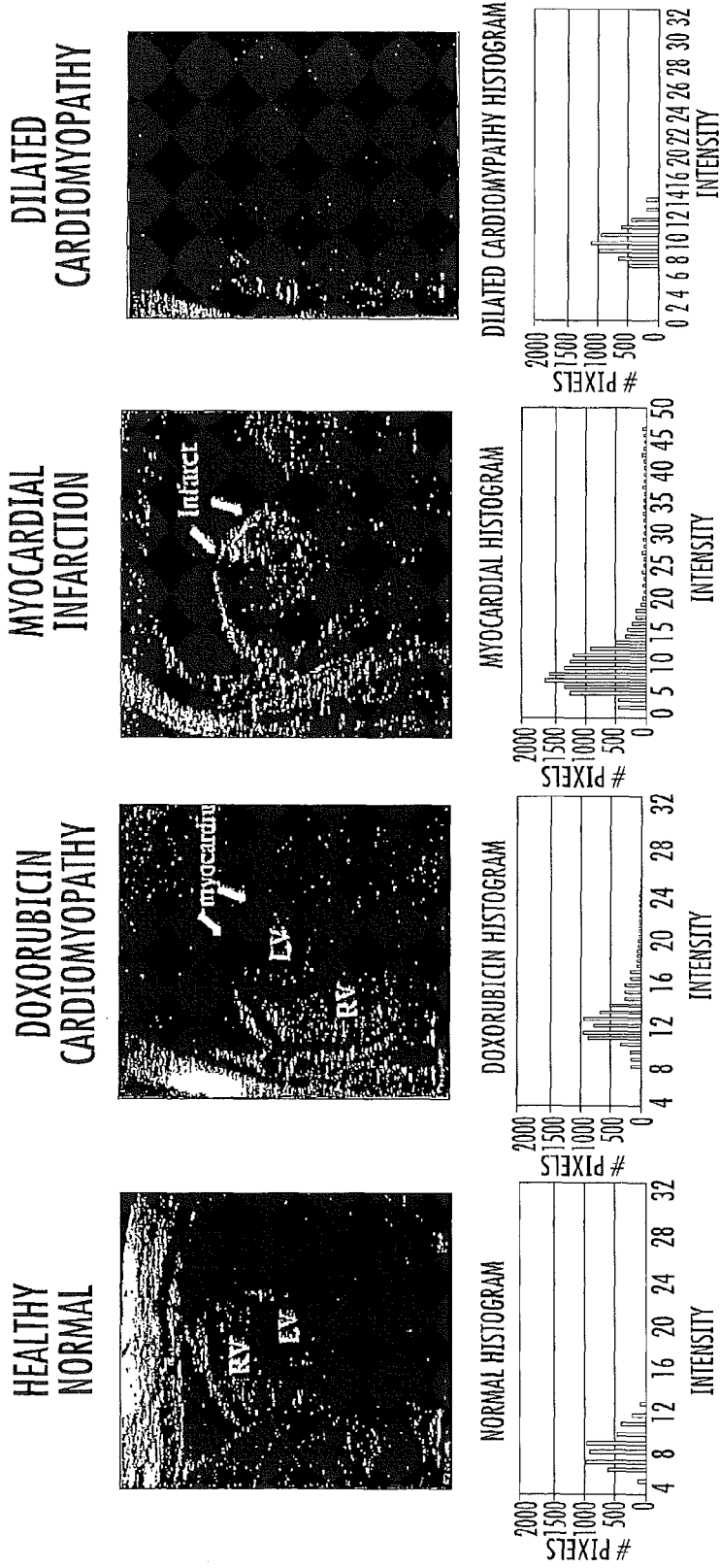
FIG. 7 are delayed enhancement MRI images in a middle (mid-plane) short axis view of the left ventricle with corresponding intensity histograms.

FIG. 7 shows exemplary delayed enhancement MR images (top panels) in a middle short axis view of the LV. The myocardium is gray and the blood pool is white. The number (y-axis) and intensity (x-axis) of voxels within the ROI (darkline) 20 minutes after contrast administration are displayed in the bottom panels. The contrast is taken up by all myocytes, but 20 minutes after administration, it is not cleared from necrotic cells. As shown, the mean intensity of contrast uptake is low in the healthy normal patient (far left) and highest in the patient with an infarct (third from left). An intermediate mean intensity is displayed on the histogram associated with the doxorubicin cardiomyopathy patient (second from left).

To determine the utility of MRI assessments of the location and magnitude of gadolinium contrast uptake 20 minutes after intravenous administration, a cross-sectional study in 4 groups of age (range 35 to 50 years) and gender matched participants was performed. These included:
a) (Group I): 4 subjects (1M,3F) without medical illness, taking no cardiac medications, and with normal LV systolic and diastolic function by MRI,
b) (Group II): 3 patients (3F) without coronary arterial luminal narrowings on contrast coronary angiography but with poor LV ejection fraction (<35%) and congestive heart failure secondary to doxorubicin administration,
c) (Group III): 3 patients (2M,1F) without coronary arterial luminal narrowings on contrast coronary angiography and with poor LV ejection fraction (<35%) and congestive heart failure secondary to an idiopathic dilated cardiomyopathy, and
d) (Group IV): 3 patients (2M,1F) with LV dysfunction secondary to an ischemic cardiomyopathy and prior ST-segment elevation myocardial infarction.

Figure 8:
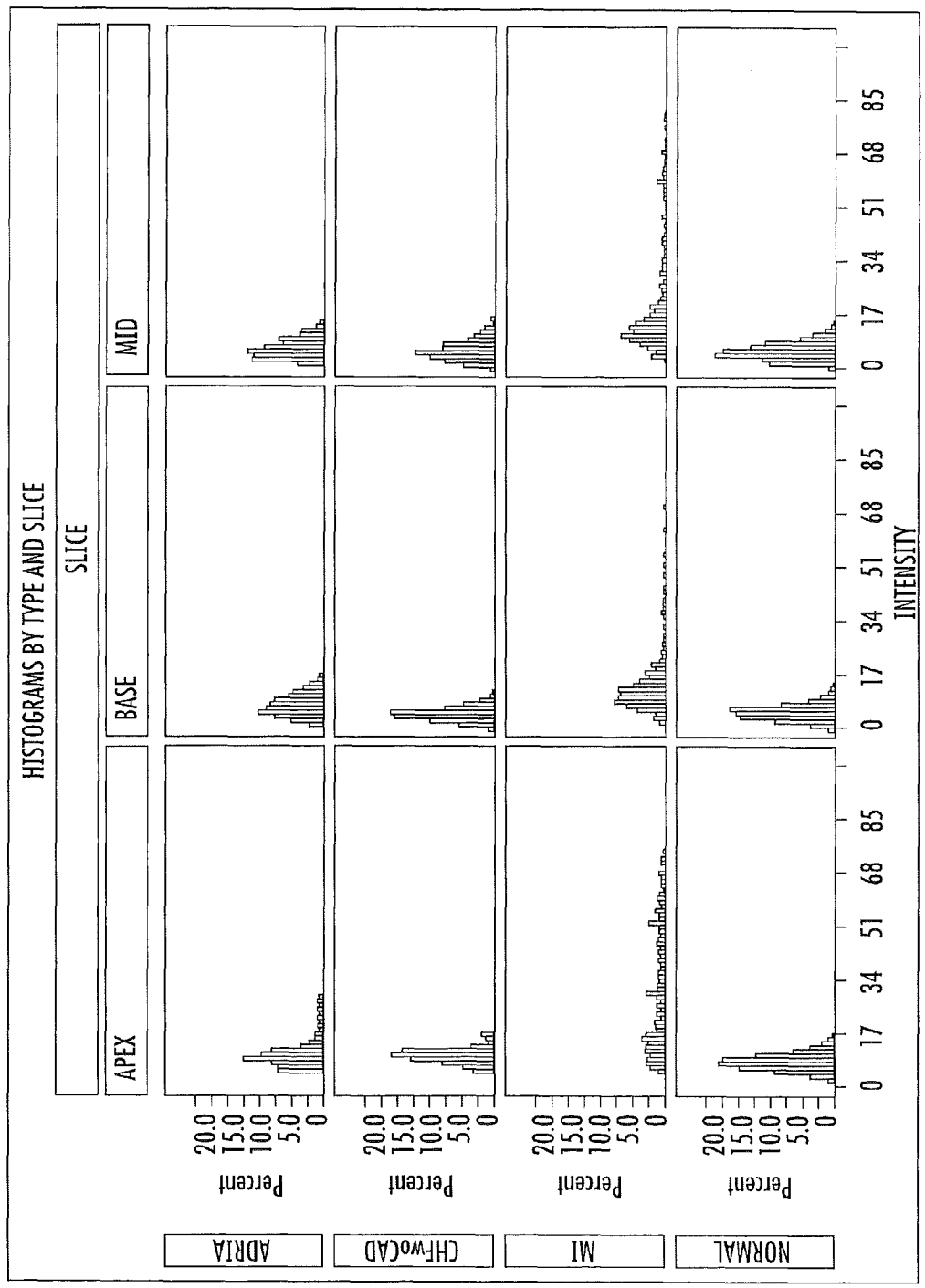
FIG. 8 are intensity histograms of voxels within a region of interest (ROI)

A middle short axis image and the distribution of intensities of voxels within the image from one subject in each group is displayed in FIG. 7, and the distributions of voxel intensities within all of the slices from all of the participants are displayed in FIG. 8.

FIG. 8 shows the percentage (y-axis) and intensity (x-axis) of voxels within ROIs from all participants in the cross-sectional sampling of subjects 20 minutes after contrast administration. As displayed in FIG. 7, an increased percentage of intensities in the 15 to 30 percent range are displayed in patients with cardiomyopathy due to chemotherapy administration compared to normal age matched controls. This pattern of intensities appears different from that seen in patients with an ischemic cardiomyopathy.

To determine the relationship between the pattern of high intensity pixels within each slice of the left ventricle, an auto-correlation statistic was used. The serial auto-correlation measure (I) is defined as follows. If $\delta_{ij}$ is a weighting function of the distance between pixels i and j, n be the number of pixels, and $x_i$ be the intensity for the $i^{th}$ pixel, then $$I = n \frac{\sum_{ij} \delta_{ij}(x_i - \bar{x})(x_j - \bar{x})}{\left(\sum_{ij} \delta_{ij}\right)\left(\sum_{i}(x_i - \bar{x})^2\right)}.$$

Equation (4)

wherein I is a measure of serial autocorrelation and is higher when adjacent pixels are both higher or lower than the mean (Ripley, 1981). In practice, the expression $$\delta_{ij} = \exp\left(-\frac{1}{2}d(x_i, x_j)\right)$$

has been used, where $d(x_i,x_j)$ is the Euclidian distance between points $x_i$ and $x_j$.

Figure 9:
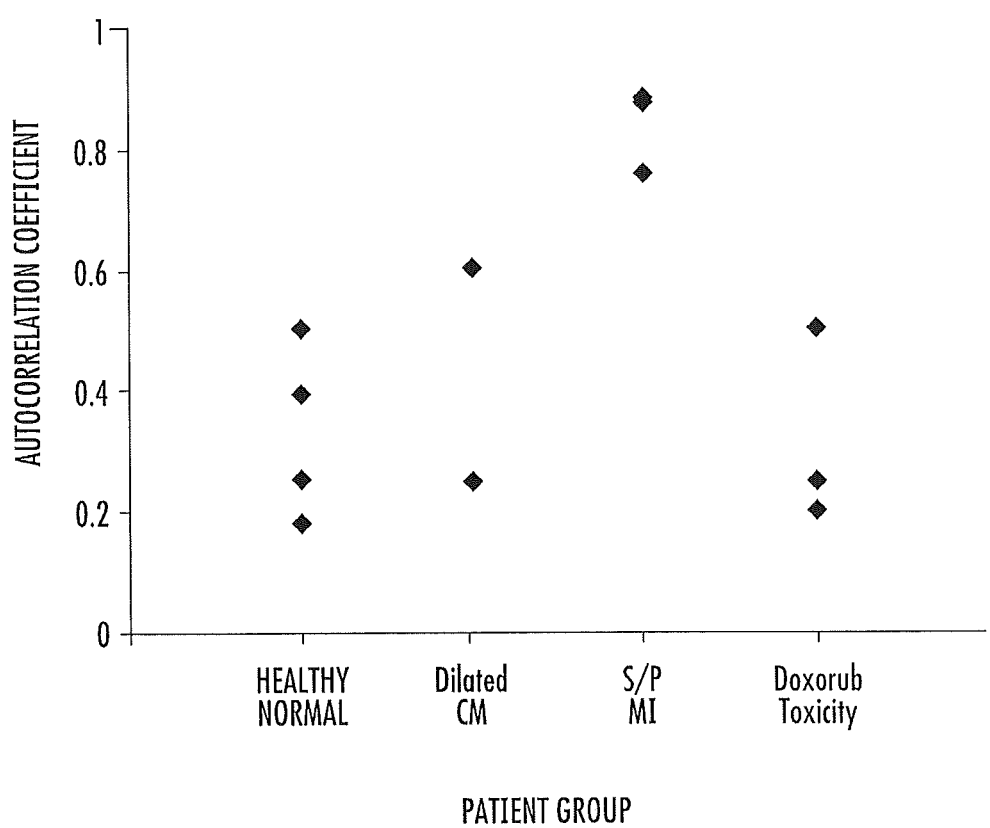
FIG. 9 is a graph of auto-correlation measures for study patients.

Using this form of analysis a high value indicates pattern clustering within the ROI, and a low value is more indicative of a random association. As shown in FIG. 9, the heightened signal intensities associated with MI were tightly clustered in the infarct zone, whereas those associated with doxorubicin toxicity were scattered throughout the LV. The pattern of contrast uptake within the LV in patients with cardiomyopathy secondary to doxorubicin administration was random and significantly different (p<0.001) from the pattern of high signal intensity voxels associated with myocardial necrosis secondary to myocardial infarction.

To determine if contrast enhancement is associated with a fall in LVEF in individuals receiving chemotherapy, a baseline MRI examination was performed in patients prior to initiation of chemotherapy, then additional MRI examinations were performed according to the research study protocol. Echocardiography exams were also performed to monitor patient left ventricular function between MRI examinations. One subject had developed dyspnea and received an echocardiogram to determine LVEF. The subject had a fall in LVEF from 55% to 48%. This individual underwent MRI testing and image analysis. The image analysis of this subject was compared to one other subject who had not developed a drop in LVEF during course of chemotherapy regimen. Images and the voxel intensities in the middle short axis view from the patients are displayed in FIG. 10.

Figure 10:
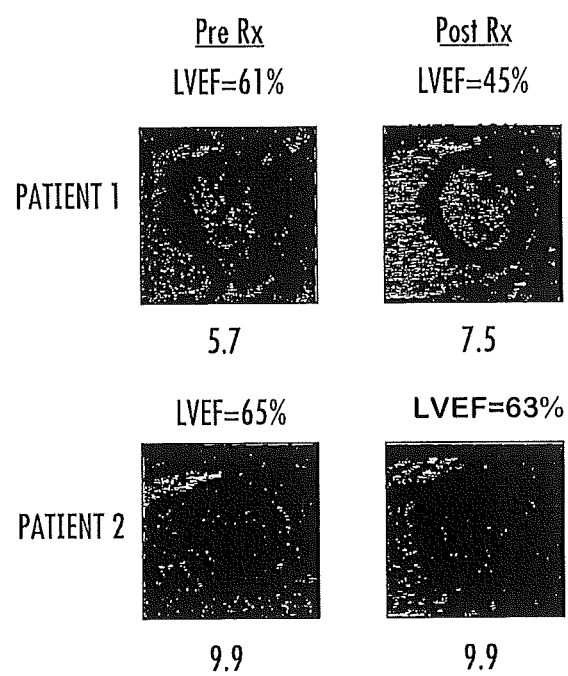
FIG. 10 are images and mean voxel intensities for two separate patients.

FIG. 10 illustrates images and mean voxel intensities at two time points in two separate patients while receiving chemotherapy, one of which developed dyspnea during the course of chemotherapy. Pre-treatment images in both patients are displayed on the left and post-treatment images are displayed on the right. Mean voxel intensities for the ROI within the image are displayed under the image. In patient 1 that developed a fall in LVEF (Top panels), heightened contrast uptake and signal intensity occurred in the second exam after receipt of 400 mg/m² of anthracyclines for treatment of breast cancer. In the second patient (Bottom panels), no fall in LVEF occurred and the uptake pattern showed no significant change. As shown, in the individual with a fall in LVEF, there was a significant increase in the intensity of voxels within the LV in the second exam compared to the first, whereas in the individual without a fall in LVEF, there was no marked change on the second exam.

Figure 11:
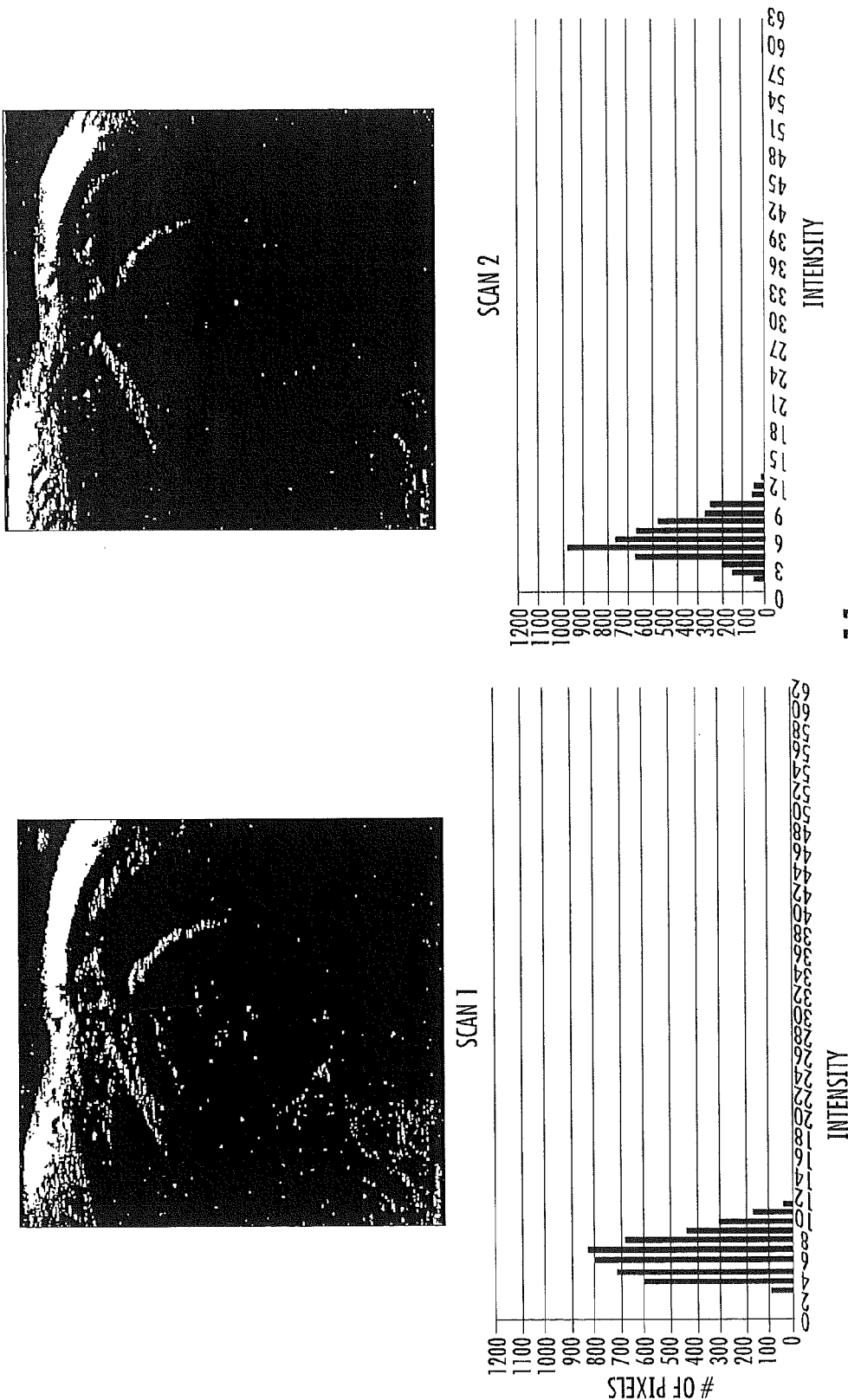
FIG. 11 are middle short axis views acquired twenty-one days apart for a patient.

To determine the variance of MRI delayed enhancement voxel intensities over time in participants without a substantive change in their medical condition, four individuals were studied twice after contrast administration over a two week period. Images from one of the participants are shown in FIG. 11, and data from both sample points in all four individuals is shown in Table 1.

TABLE 1

In four participants, MRI intensity (mean ± standard deviation) and LVEF.

|  | Day 1 | Day 21 |  |
| --- | --- | --- | --- |
| LVEF | 0.67 ± 0.04 | 0.64 ± 0.04 | p = NS |
| Mean intensity | 6.64 ± 1.15 | 6.60 ± 0.96 | p = NS |

FIG. 11 illustrates middle left ventricular short axis views acquired 21 days apart in an individual without a change in their condition. Note the near exact replication of the slice position on the second acquisition using software discussed elsewhere herein. Twenty minutes after contrast administration, the signal intensity within the ROIs was not significantly different (5.8 vs. 6.1 (p=NS)). MRI examinations with this technique may be acquired reproducibly over time.

There was little change in the uptake patterns of contrast in the subjects between the first and second exam, and for the four individuals measured at two points in time, the correlation between the 2 measurements was excellent (y=0.87x+1.2, R²=0.96).

Based on the above data, it appears that delayed enhancement MRI uptake patterns of contrast are elevated in patients with cardiomyopathy secondary to chemotherapy induced cardiotoxicity compared to age and gender matched control subjects. The pattern of this contrast uptake is diffuse and randomly distributed throughout the left ventricle in a fashion that is distinctly different from myocellular injury observed in patients sustaining a myocardial infarction. In the project involving two patients receiving chemotherapy, heightened contrast uptake occurred coincident with a fall in LVEF in one, but not the other that did not develop a fall in LVEF. Such a methodology and analysis methods may be highly reproducible and exhibit low intraobserver variability.

Figure 15:
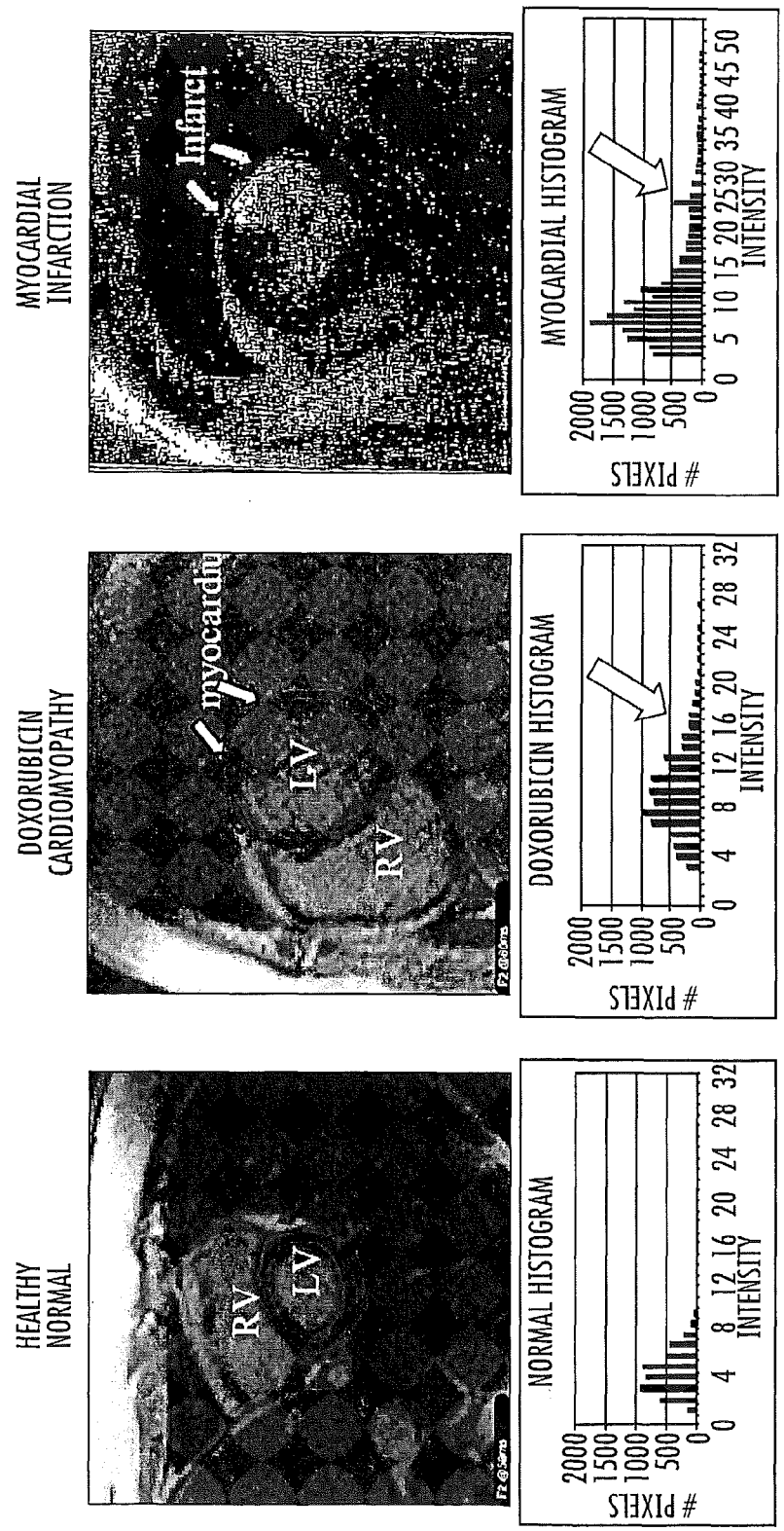
FIG. 15 are delayed enhancement CMR images in a middle (mid-plane) short axis view of the left ventricle with corresponding intensity histograms (lower panels) of number (y-axis) and intensity (x-axis) of voxels within the region of interest noted in the short axis view (top panel).

To further illustrate the utility of CMR assessments of the LV (to predict a future drop in LVEF), the location and magnitude of gadolinium contrast uptake 20 minutes after intravenous administration were assessed in a cross-sectional study of three groups of age (range 35-50) and gender matched participants. The participants included healthy subjects (Group I, n=4), patients with cardiomyopathy due to chemotherapy (Group II, n=3), and patients sustaining a prior myocardial infarction (Group III, n=3). A middle short axis image and the distribution of LV myocardial voxel intensities within the image from one subject in each group is shown in FIG. 15. Aggregate data are displayed in FIG. 16 in which the voxel intensities for the three slice positions of the left ventricle (apex, middle, and basal slice) demonstrate a similar pattern of signal intensities as shown, for example, in the middle pane of FIG. 16.

FIG. 15 shows delayed enhancement CMR images (top panels) in a middle short axis view of the left ventricle. The left image is of healthy/normal tissue, the center image is from a patient with doxorubicin cardiomyopathy, and the right image is from a patient with an infarct. In the images, the myocardium is gray and the blood pool is white. Beneath the images, histograms plotting the number (y-axis) and intensity (x-axis) of voxels within the region of interest (corresponding to regions in the lines on the respective images) on the cardiac tissue shown on the upper panels delineating the LV myocardium about 20 minutes after contrast administration are displayed. The contrast is taken up by all myocytes, but at about 20 minutes after administration; it is not cleared from abnormal tissue. As shown by the arrows on the histogram, high intensity voxels are noted in the patient with doxorubicin injury and prior myocardial infarction compared to healthy "normal" patient.

Figure 16:
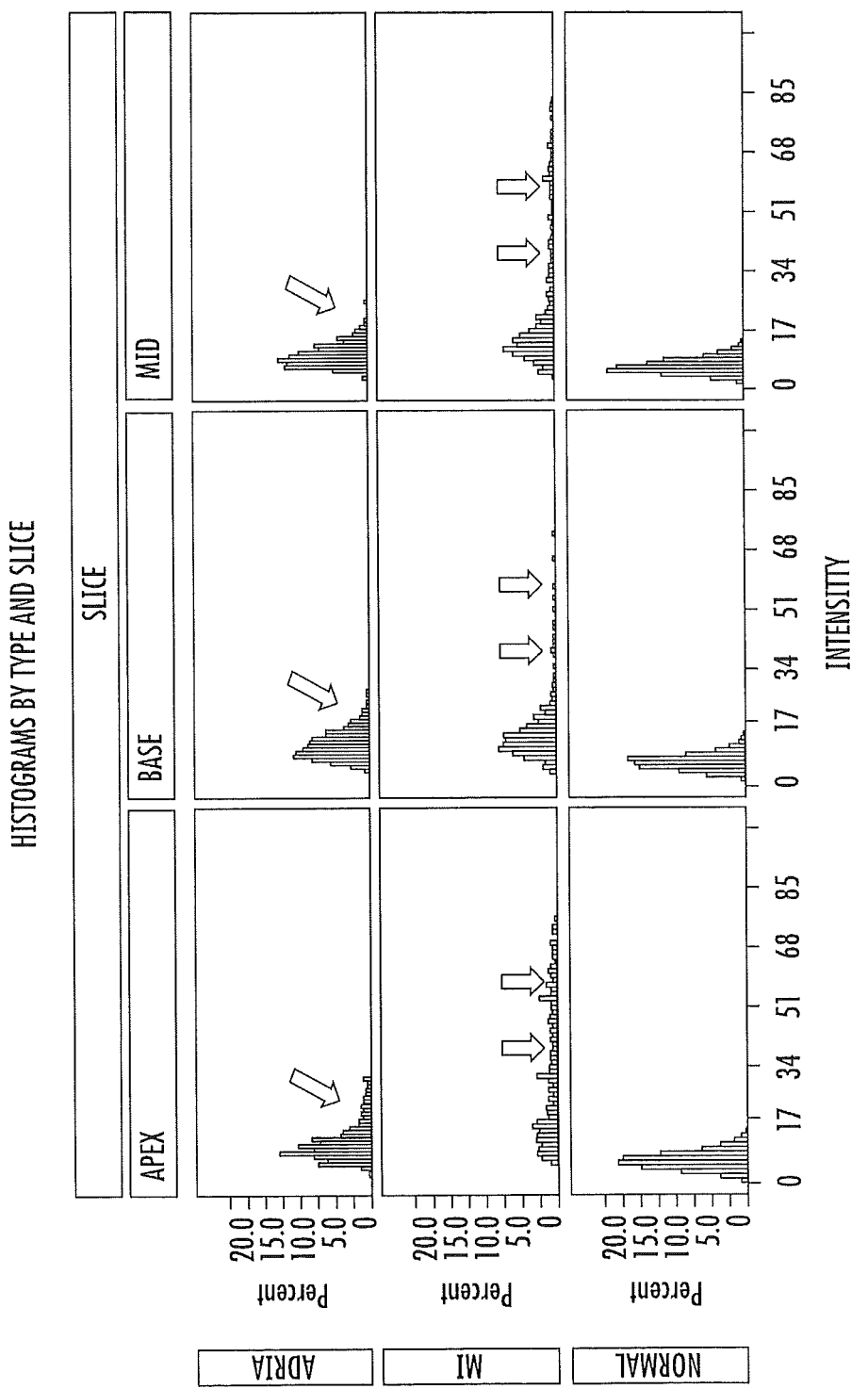
FIG. 16 are aggregate histograms graphs of percent versus intensity of voxels by type and slice according to embodiments of the present invention.

FIG. 16 illustrates aggregate histograms displaying percentage (y-axis) and intensity (x-axis) of voxels within regions of interest from a series of patients about 20 minutes after contrast administration. As displayed in FIG. 16, an increased percentage of intensities (dark arrows) are observed in patients with cardiomyopathy (labeled "Adria" in FIG. 16) due to doxorubicin administration as compared to normal age matched controls. Very high intensity voxels (lighter color or gray arrows in the mid panel histograms of FIG. 16) are noted in the slices from patients with prior myocardial infarction (MI) as compared to "normal" and "Adria" histograms.

As discussed above with respect to FIG. 9, the relationship between the pattern of high intensity voxels within each slice of the left ventricle was determined using correlation statistics (autocorrelation statistics). See, e.g., B. D. Ripley, *Spatial Statistics*, Wiley: NY, 1981. Using this form of analysis, a high number (the higher the autocorrelation coefficient) indicates pattern clustering of the high signal intensities within the region of interest, and a low number is more indicative of a random association.

Figure 17:
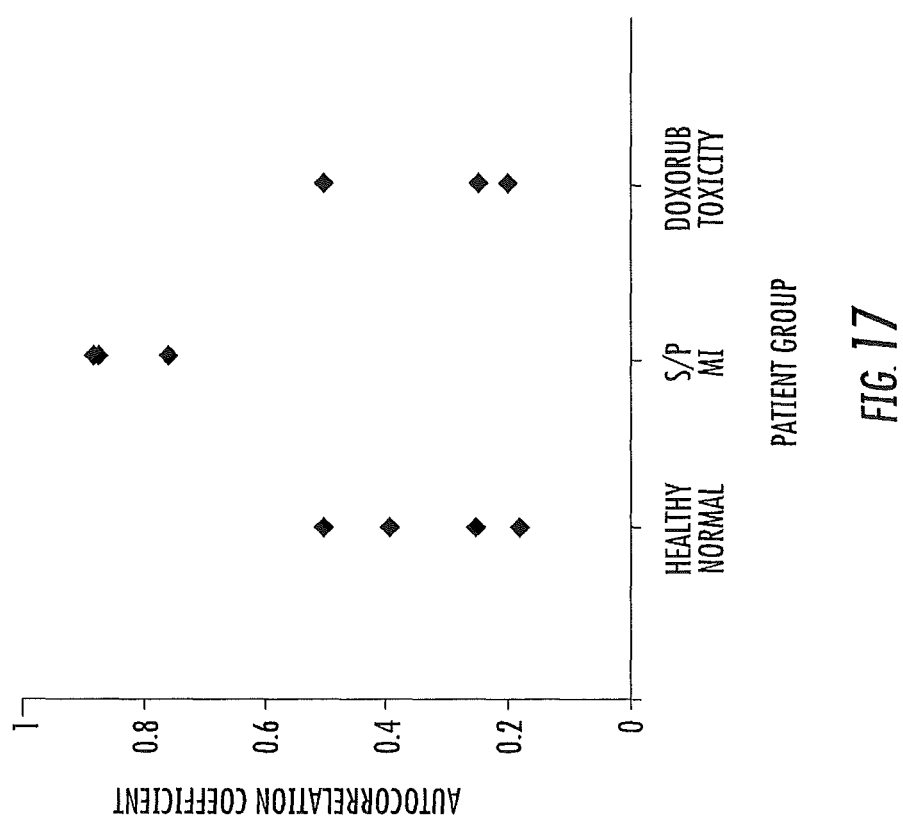
FIG. 17 is a graph of auto-correlation measures for study patients.

As shown in the graph of FIG. 17, the pattern of contrast uptake within the left ventricle in patients with cardiomyopathy secondary to doxorubicin administration was random and significantly different (p<0.001) from the pattern of high signal intensity voxels associated with myocardial necrosis secondary to myocardial infarction. In addition, the pattern of high signal intensity voxels was in a distribution similar to the random pattern found in the normal individuals without myocardial injury. The serial autocorrelation measure (I) is as was discussed above with respect to FIG. 9 and Equation (4). As shown in FIG. 17, the heightened signal intensities associated with myocardial infarction were tightly clustered in the infarct zone, whereas those associated with doxorubicin toxicity were scattered throughout the left ventricle.

Figure 18:
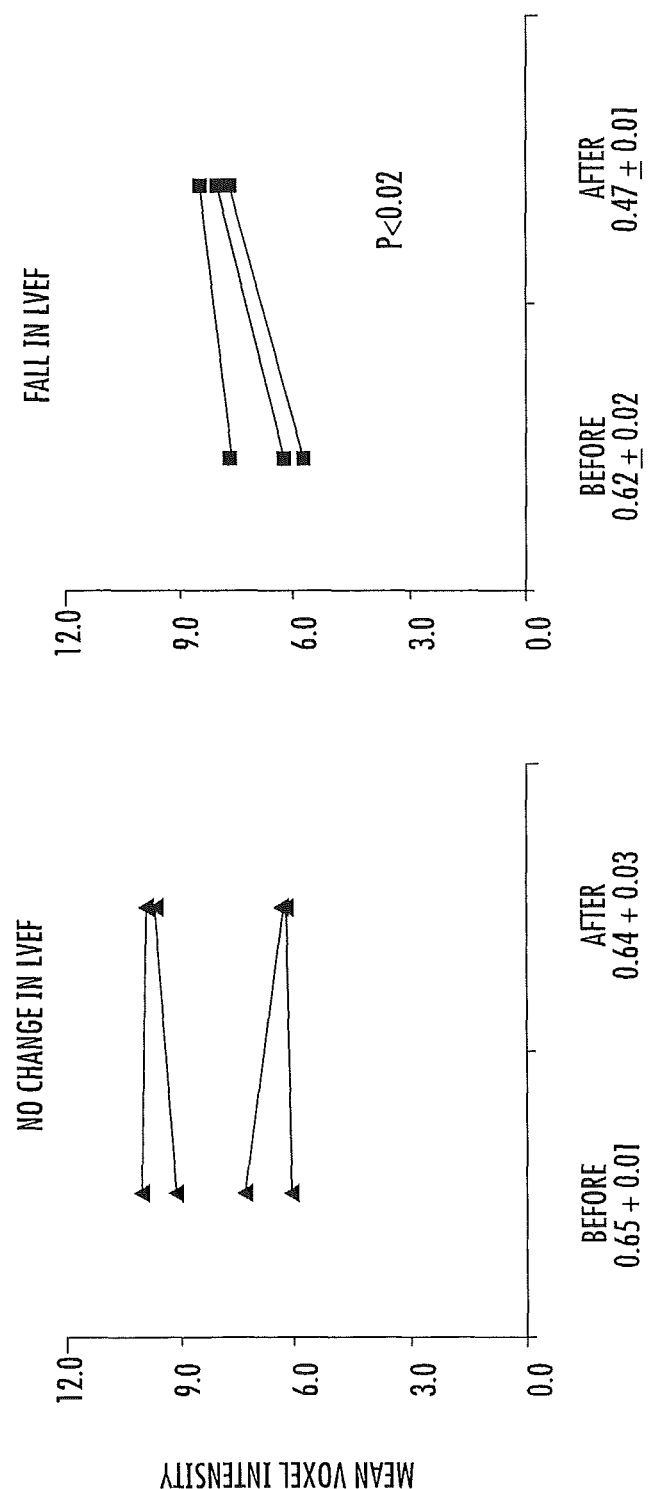
FIG. 18 are plots of mean pixel intensities of the left ventricle myocardium in a short axis plane versus LVEF before and after receipt of chemotherapy in patients without a change in LVEF (left graph) and patients that developed a fall in LVEF (right graph)

To determine if contrast enhancement is associated with a decrease in LVEF in individuals receiving doxorubicin for breast cancer, a baseline CMR exam was obtained in eight patients prior to and during receipt of 2-4 months of chemotherapy. One subject died before completing the protocol. Data from the remaining seven (7) subjects is shown in FIG. 18. Table 2 provides additional data regarding the time course of mean signal intensity from these patients.

FIG. 18 illustrates plots displaying the mean pixel intensities of the LV myocardium in a short axis plane before and after receipt of chemotherapy in 4 subjects without a change in LVEF (left plot) and 3 subjects that developed a decrease in LVEF (right plot). During the study, individuals receiving chemotherapy were studied at 1 month, and 2-4 months after receiving chemotherapy. All subjects received doxorubicin and cytoxan in this study. Among participants that dropped and did not drop in LVEF, there was an equivalent distribution of participants receiving HERCEPTIN®, paclitaxel and 5-fluorouracil. As shown in FIG. 18, the individuals without a fall in LVEF had no substantive increase in their mean voxel intensity during receipt of breast cancer chemotherapy. However, individuals that developed a fall in LVEF developed a substantive increase in signal intensity on the later examinations. In participants with a drop versus those without a LVEF drop, there was a significant difference in the change in mean voxel intensity using a 2 sample t-test. The standard deviation of the mean voxel intensities over the course of the study for the four subjects without a change in LVEF was 0.64, similar to the reproducibility discussed with respect to FIG. 19 below. Table 2 provides additional data regarding the time course of contrasts intensity relative to LVEF decrement.

TABLE 2

Mean Intensity and LVEF in patients receiving chemotherapy

|  |  | Baseline | 1 Month | 2-4 Months |
|---|---|---|---|---|
| Patient 1 | MRI | 6.4 | 8.8 | 8.1 |
|  | LVEF | 0.64 | 0.68 | 0.48 |
| Patient 2 | MRI | 6.8 | 8.1 | 8.51 |
|  | LVEF | 0.61 | 0.59 | 0.46 |
| Patient 3 | MRI | 5.9 | 7.8 | Begun on ACE |
|  | LVEF | 0.61 | 0.47 |  |

In the three subjects, the mean signal intensity of the voxels within the myocardium changed. Data was taken from these subjects before (baseline), then after receiving a chemotherapy regimen containing doxorubicin. In one individual (patient #3), the LVEF rapidly decreased at the first exam concomitant with an increase in signal intensity. In the other individuals (patient #1, patient #2), there was an increase in mean signal intensity that preceded the decrement in LVEF by about 4-8 weeks. This human subject data suggests that there is an increase in contrast uptake prior to decrement of LVEF in human subjects that develop cardiotoxicity from chemotherapy.

To determine the reproducibility of CMR delayed enhancement voxel intensities over time in patients without a substantive change in their medical condition, four individuals were studied after contrast administration over about a 2-week period. Images were analyzed in an unpaired, blinded fashion; the correlation between the two measurements was excellent (y=0.87x+1.2, $R^2$=0.96). To determine the reproducibility of the analysis technique, ROIs were drawn twice on middle short axis images of the LV in a blinded fashion separated by a 2-month time interval. The mean intensity of the voxels was 6.38+/−0.67 on the first series of drawings and 6.35+/− on the second series. The correlation between the two measures of intensity analyzed on the same image set was excellent (y=1.01x−0.1, R2=0.99). A representative short axis slice from a participant in the reproducibility study is shown in FIG. 19.

Figure 19:
FIG. 19 are delayed contrast enhancement MRI images of middle left ventricular short axis views acquired 18 days apart in a normal individual (the anterior chest is at the top of the images) with corresponding graphs of mean voxel intensities below the respective images.
Figure 19:
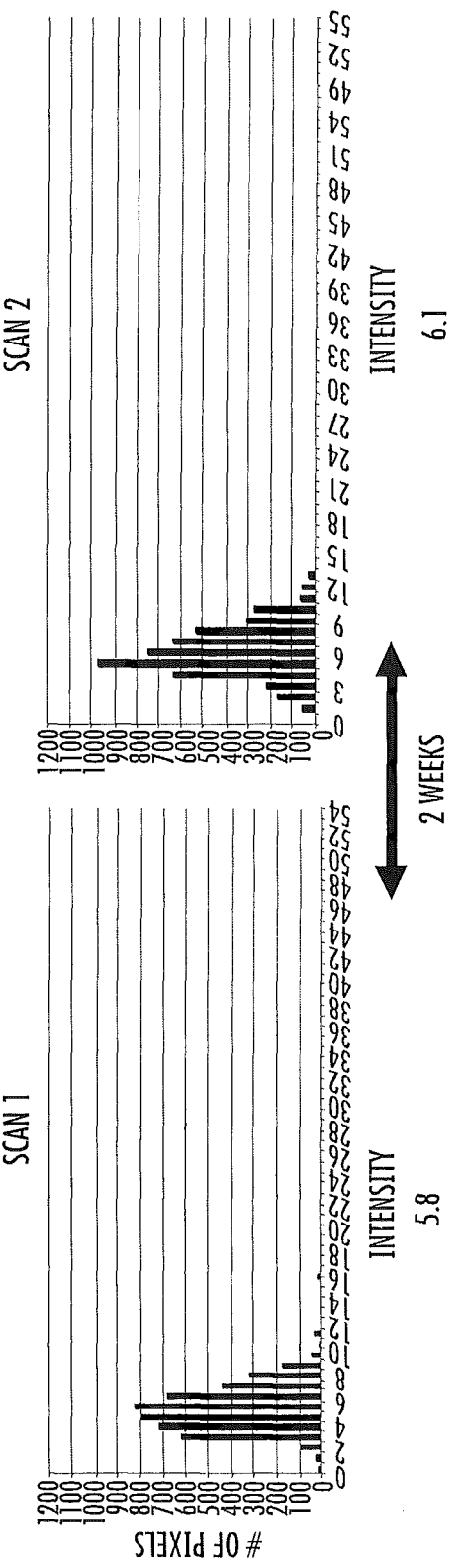

FIG. 19 illustrates middle left ventricular short axis image views acquired 18 days apart in a normal individual without a (known) change in their medical condition. The anterior chest is noted at the top of the images. In the center of the images, the LV myocardium is gray and the blood pool within the left and right ventricular cavities is generally white (or much lighter than the myocardium). Note the near exact replication of the slice position on the second acquisition using physician interactive tools that allows the physician to draw freehand, or with software GUI tools, the endo- and epi-cardial boundaries of the LV myocardium, and that can also allow a physician to define a region of interest for the background noise in the air as discussed above. About twenty minutes after contrast administration, data corresponding to the signal intensity of the voxels within the LV myocardium can be acquired as shown in the graphs beneath the images shown in FIG. 19. The signal data can be acquired, displayed, and/or stored for future or substantially concurrent (real-time) evaluation. The mean intensities (displayed beneath the graphs) were not significantly different (5.8+/−0.3 versus 6.1+/−0.3; p=NS) from one another and were highly correlated.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims.

That which is claimed is:

1. A medical system, comprising:
   a workstation comprising or in communication with a circuit for generating an image of target tissue of a patient using a measure of one or more voxel characteristic of substantially an entire population of voxels from patient images associated with the target tissue, wherein the generated image visually indicates whether there is a likelihood of a global injury, and wherein the global injury is a change in at least one of (i) tissue composition and function, (ii) tissue composition or (iii) tissue function, that is not visually detectable in the patient images and/or that is in a substantially randomly distributed pattern in the target tissue; and
   a display in communication with the circuit for displaying the generated image.

2. The workstation of claim 1, wherein the generated image is a 3-D image, and wherein the global injury is illustrated so that like colors represent like measures of the one or more voxel characteristics.

3. The workstation of claim 1, wherein the target tissue comprises at least one of brain, nerve, skeletal, skeletal muscle, liver, kidney, lung, pancreatic, endocrine, gastrointestinal and/or genitourinary tissue.

4. The workstation of claim 1, wherein the circuit is configured to electronically analyze the patient images to determine a location of respective voxels in three-dimensional space and correlate a respective measure of the one or more voxel characteristic.

5. The workstation of claim 1, wherein the target tissue is heart tissue, and wherein the global injury is associated with replacement of native myocardial tissue with fibrous tissue that results in necrosis and/or fibrosis in a substantially randomly distributed pattern or in a pattern that is not visually detectable at a resolution of the patient images.

6. The workstation of claim 5, wherein the diagnostic image is a 3-D image of at least a portion of the heart.

7. The workstation of claim 1, wherein the global injury is associated with an abnormal accumulation of material that is not in normal ratios within native tissue.

8. The workstation of claim 1, wherein the one or more voxel characteristic includes at least one of the following: intensity, color saturation, or other characteristic of individual voxels.

9. The workstation of claim 1, wherein the one or more voxel characteristic includes a relative characteristic.

10. The workstation of claim 1, wherein the circuit is configured to detect whether there is a random pattern of like measures of the one or more voxel characteristic distributed over the regions of interest, and wherein the target tissue is one of brain, nerve, skeletal, skeletal muscle, liver, kidney, lung, pancreatic, endocrine, gastrointestinal and/or genitourinary tissue.

11. The workstation of claim 1, wherein the patient images comprise non-contrast agent based MRI image slices, and wherein the circuit is configured to analyze the MRI image slices to generate the image.

12. The workstation of claim 1, wherein the circuit is configured to analyze MRI image data obtained from contrast-agent based MRI image slices to generate the image.

13. The workstation of claim 1, wherein the one or more voxel characteristic includes a shape of a histogram.

14. The workstation of claim 1, wherein the generated image visually emphasizes abnormal tissue characteristics and/or function using the measure of the one or more voxel characteristic and an associated x, y and z coordinate to thereby provide an early detection of a global injury.

15. The workstation of claim 1, wherein the patient images comprise cardiac MRI image slices, and wherein the target tissue is cardiac tissue and the generated image is a 3-D image of the heart.

16. The workstation of claim 15, wherein the measure of the one or more voxel characteristics includes quantified measures of voxel intensity, and wherein the generated image visually accentuates regions of impaired or dead cells in graduated shades of color or different colors for different voxel intensities.

17. The workstation of claim 1, wherein the patient images comprise cardiac MRI image slices, wherein the target tissue is cardiac tissue and the generated image is a 3-D image of a patient's heart, and wherein the generated image visualizes cell injury associated with inflammation or accumulation of water around cells in the heart which can inhibit contractility and impair cardiac function.

18. The workstation of claim 1, wherein the measure of the one or move voxel characteristic includes a measure of voxel intensity, wherein the patient images comprise MRI image slices, wherein the target tissue is cardiac tissue and the generated image is a 3-D image of the heart, and wherein the circuit is configured to generate the image to visually show location and voxels with intensity measures, with like values having like colors.

19. The workstation of claim 1, wherein the patient images comprise MRI image slices, wherein the patient image slices include slices of an apical, middle and basal portion of the heart.

20. The workstation of claim 1, wherein the patient images comprise MRI image slices, and wherein the circuit is configured to render the generated image to quantify a presence of a target or molecular process and/or define metabolic pathways that are functioning within tissue in an organ system.

21. The workstation of claim 1, wherein the circuit is configured to determine whether the global injury is associated with an increased risk of cardiac injury associated with a decrease in heart function.

22. The workstation of claim 1, wherein the patient images comprise cardiac MRI image slices, and wherein the global injury in the generated image is at least one of the following: a radiation-induced global injury, an environmental exposure-induced global injury, a venom-induced global injury, or a drug- or toxin-induced global injury.

23. The workstation of claim 1, wherein the patient images comprise cardiac Magnetic Resonance (cMR) images, wherein the circuit is configured to electronically interrogate substantially all voxels within a contiguous series of short axis slice positions spanning an apex to a base in the cMR images and identify the measure of the one or more voxel characteristic and a corresponding x, y and z coordinate of each respective voxel in three-dimensional space, and wherein the generated image is a non-invasive biopsy image of the patient's heart.

24. The workstation of claim 1, wherein the circuit is configured to electronically distinguish cardiac injury associated with myocardial infarct from cardiac injury associated with cardiotoxicity.

* * * * *